United States Patent [19]

Kahn

[11] Patent Number: 5,693,325
[45] Date of Patent: Dec. 2, 1997

[54] PEPTIDE VACCINES AND METHODS RELATING THERETO

[75] Inventor: Michael Kahn, Bellevue, Wash.

[73] Assignee: Molecumetics, Ltd., Bellevue, Wash.

[21] Appl. No.: 213,124

[22] Filed: Mar. 15, 1994

[51] Int. Cl.$^6$ .................. A61K 39/21; A61K 39/385
[52] U.S. Cl. .................. 424/188.1; 424/185.1; 424/188.1; 424/193.1; 424/194.1; 424/196.11; 530/317; 530/323; 530/403
[58] Field of Search .................. 530/323, 317, 530/345, 403; 424/185.1, 188.1, 193.1, 194.1, 196.11

[56] References Cited

U.S. PATENT DOCUMENTS 5,334,702   8/1994   Greene et al. .................. 530/323

FOREIGN PATENT DOCUMENTS

| | | | |
|---|---|---|---|
| WO 90/13564 | 11/1990 | WIPO. | |
| WO 92/13878 | 8/1992 | WIPO | C07K 5/02 |
| WO 92/20704 | 11/1992 | WIPO | C07K 5/00 |
| WO 94/03494 | 2/1994 | WIPO | C07K 15/00 |

OTHER PUBLICATIONS

Sato et al (1993) Bioorg. Med. Chem. Lett, 3(6):1277–1282.
Chen et al., "Design and Synthesis of a CD4 beta–turn mimetic that inhibits human immunodeficiency virus envelope glycoprotein gp120 binding and infection of human lymphocytes," Proc. Natl. Acad. Sci. USA 89:5872–5876, 1992.
Johnson et al., "Hypothesis: Conformational rearrangements required of the V3 loop of HIV–1 gp120 for proteolytic cleavage and infection," FEBS Letters 337:4–8, 1994.
Ahlers et al., "Construction of an HIV–1 Peptide Vaccine Containing a Multideterminant Helper Peptide Linked to a V3 Loop Peptide 18 Inducing Strong Neutralizing Antibody Responses in Mice of Multiple MHC Haplotypes after Two Immunizations," J. Immunol. 150(12):5647–5665, 1993.
Tolman et al., "Cyclic V3–loop–related HIV–1 conjugate vaccines," International Journal of Peptide & Protein Research 41:455–466, 1993.
Warren et al., "Examination of Sera from Human Immunodeficiency Virus Type 1 (HIV–1)–Infected Individuals for Antibodies Reactive with Peptides Corresponding to the Principal Neutralizing Determinant of HIV–1 gp120 and for In Vitro Neutralizing Activity," J. Virol. 66(9):5210–5215, 1992.
Lasky et al., "Delineation of a Region of the Human Immunodeficiency Virus Type 1 gp120 Glycoprotein Critical for Interaction with the CD4 Receptor," Cell 50:975–985, 1987.
Palker et al., "Polyvalent Human Immunodeficiency Virus Synthetic Immunogen Comprised of Envelope gp120 T Helper Cell Sites and B Cell Neutralization Epitopes", J. Immunol. 142(10):3612–3619, 1989.
Leonetti et al., "Immunization with a Peptide Having Both T Cell and Conformationally Restricted B Cell Epitopes Elicits Neutralizing Antisera Against a Snake Neurotoxin", J. Immunol. 145(12):4214–4221, 1990.

Wyatt et al., "Relationship of the Human Immunodeficiency Virus Type 1 gp120 Third Variable Loop to a Component of the CD4 Binding Site in the Fourth Conserved Region", J. Immunol. 66(12):6997–7004, 1992.
Cease et al., "Helper T–cell antigenic site identification in the acquired immunodeficiency syndrome virus gp120 envelope protein and induction of immunity in mice to the native protein using a 16–residue synthetic peptide", Proc. Natl. Acad. Sci. USA 84:4249–4253, 1987.
Sastry et al., "Rapid in Vivo Induction of HIV–Specific CD8+ Cytotoxic T Lymphocytes by a 15–Amino Acid Unmodified Free Peptide from the Immunodominant V3–Loop of GP 120", Virology 188:502–509, 1992.
Henrickson et al., "Neutralizing epitopes of human parainfluenza virus type 3 are conformational and cannot be imitated by synthetic peptides", Vaccine 9:243–249, 1991.
Muller et al., "Antigenic properties and protective capacity of a cyclic peptide corresponding to site A of influenza virus haemagglutinin", Vaccine 8:308–314, 1990.
Knossow et al., "Three–dimensional structure of an antigenic mutant of the influenza virus haemagglutinin", Nature 311:678–680, 1984.
Van Noort and van der Drift, "The Selectivity of Cathepsin D Suggests an Involvement of the Enzyme in the Generation of T–cell Epitopes", The Journal of Biological Chemistry 264(24): 14159–14164, 1989.
Zaloom and Roberts, "Preparation of Azido Derivatives from Amino Acids and Peptides by Diazo Transfer", J. Org. Chem. 46:5173–5176, 1981.
Milich, "Synthetic T and B Cell Recognition Sites: Implications for Vaccine Development", Advances in Immunology 45:204–209 and 240–251, 1989.
Arnon and Regenmortel, "Structural basis of antigenic specificity and design of new vaccines", The FASEB Journal 6:3265–3274, 1992.
Berzofsky, "Mechanisms of T Cell Recognition with Application to Vaccine Design," Molecular Immunology 28(3):217–223, 1991.

Primary Examiner—Ponnathapura Achutamurthy
Attorney, Agent, or Firm—Seed and Berry LLP

[57] ABSTRACT

There are disclosed peptide vaccines and methods related thereto for generating a protective immune response in warm–blooded animals. The peptide vaccines comprise a conformationally constrained reverse–turn mimetic, a T cell stimulatory peptide, and a cleavable linker covalently joining the conformationally constrained reverse–turn mimetic and the T cell stimulatory peptide. The conformationally constrained reverse-turn mimetic mimics the three-dimensional structure of an antigenic determinant of a native pathogenic protein and is capable of binding to a B cell. Upon binding to a B cell, the peptide vaccine is internalized, and the T cell stimulatory peptide is released from the conformationally constrained reverse-turn mimetic by cleavage of the cleavable linker. The T cell stimulatory peptide is then expressed on the surface of the B cell in association with class I or II MHC molecules, thus inducing T cell activity and generating a protective immune response.

8 Claims, No Drawings

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( x i ) SEQUENCE DESCRIPTION: SEQ ID NO:1:

```
Arg Lys Arg Ile His Ile Gly Pro Gly Arg Ala Phe
1               5                   10
```

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Gly Pro Gly Arg
1
```

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( x i ) SEQUENCE DESCRIPTION: SEQ ID NO:3:

```
Lys Arg Gly Pro Gly Ser Gly
1               5
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

```
Gln Ile Ile Asn Met Trp Gln Lys Val Gly
1               5                   10
```

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( x i ) SEQUENCE DESCRIPTION: SEQ ID NO:5:

```
Lys Gln Ile Ile Asn Met Trp Gln Glu Val Gly Lys Ala Met Tyr Ala
1               5                   10                  15
```

( 2 ) INFORMATION FOR SEQ ID NO:6:

( i ) SEQUENCE CHARACTERISTICS:
- ( A ) LENGTH: 15 amino acids
- ( B ) TYPE: amino acid
- ( C ) STRANDEDNESS:
- ( D ) TOPOLOGY: linear ( x i ) SEQUENCE DESCRIPTION: SEQ ID NO:6:

Gly Pro Lys Glu Pro Phe Arg Asp Tyr Val Asp Arg Phe Tyr Lys
1               5                   10                  15

( 2 ) INFORMATION FOR SEQ ID NO:7:

( i ) SEQUENCE CHARACTERISTICS:
- ( A ) LENGTH: 26 amino acids
- ( B ) TYPE: amino acid
- ( C ) STRANDEDNESS:
- ( D ) TOPOLOGY: linear ( x i ) SEQUENCE DESCRIPTION: SEQ ID NO:7:

Gly Pro Lys Glu Pro Phe Arg Asp Tyr Val Asp Arg Phe Tyr Lys Thr
1               5                   10                  15

Leu Arg Ala Glu Gln Ala Ser Gln Glu Val
            20                  25

( 2 ) INFORMATION FOR SEQ ID NO:8:

( i ) SEQUENCE CHARACTERISTICS:
- ( A ) LENGTH: 13 amino acids
- ( B ) TYPE: amino acid
- ( C ) STRANDEDNESS:
- ( D ) TOPOLOGY: linear ( x i ) SEQUENCE DESCRIPTION: SEQ ID NO:8:

His Glu Asp Ile Ile Ser Leu Trp Asn Gln Ser Leu Lys
1               5                   10

( 2 ) INFORMATION FOR SEQ ID NO:9:

( i ) SEQUENCE CHARACTERISTICS:
- ( A ) LENGTH: 17 amino acids
- ( B ) TYPE: amino acid
- ( C ) STRANDEDNESS:
- ( D ) TOPOLOGY: linear ( x i ) SEQUENCE DESCRIPTION: SEQ ID NO:9:

Tyr Lys Lys Val Trp Arg Asp His Arg Gly Thr Ile Ile Glu Arg Gly
1               5                   10                  15

Cys ( 2 ) INFORMATION FOR SEQ ID NO:10:

( i ) SEQUENCE CHARACTERISTICS:
- ( A ) LENGTH: 15 amino acids
- ( B ) TYPE: amino acid
- ( C ) STRANDEDNESS:
- ( D ) TOPOLOGY: linear ( x i ) SEQUENCE DESCRIPTION: SEQ ID NO:10:

Ala Val Tyr Thr Arg Ile Met Met Asn Gly Gly Arg Leu Lys Arg
1               5                   10                  15

( 2 ) INFORMATION FOR SEQ ID NO:11:

( i ) SEQUENCE CHARACTERISTICS:
- ( A ) LENGTH: 12 amino acids
- ( B ) TYPE: amino acid
- ( C ) STRANDEDNESS:
- ( D ) TOPOLOGY: linear ( x i ) SEQUENCE DESCRIPTION: SEQ ID NO:11:

Lys Gln Ile Arg Asp Ser Ile Thr Glu Glu Trp Ser
1               5                      10

( 2 ) INFORMATION FOR SEQ ID NO:12:

( i ) SEQUENCE CHARACTERISTICS:
       ( A ) LENGTH: 27 amino acids
       ( B ) TYPE: amino acid
       ( C ) STRANDEDNESS:
       ( D ) TOPOLOGY: linear ( x i ) SEQUENCE DESCRIPTION: SEQ ID NO:12:

Gly Pro Lys Glu Pro Phe Arg Asp Tyr Val Asp Arg Phe Tyr Lys Arg
1               5                      10                      15

Lys Arg Ile His Ile Gly Pro Gly Arg Ala Phe
                20                  25

( 2 ) INFORMATION FOR SEQ ID NO:13:

( i ) SEQUENCE CHARACTERISTICS:
       ( A ) LENGTH: 28 amino acids
       ( B ) TYPE: amino acid
       ( C ) STRANDEDNESS:
       ( D ) TOPOLOGY: linear ( x i ) SEQUENCE DESCRIPTION: SEQ ID NO:13:

Gly Pro Lys Glu Pro Phe Arg Asp Tyr Val Asp Arg Phe Tyr Leu Lys
1               5                      10                      15

Arg Lys Arg Ile His Ile Gly Pro Gly Arg Ala Phe
                20                  25

( 2 ) INFORMATION FOR SEQ ID NO:14:

( i ) SEQUENCE CHARACTERISTICS:
       ( A ) LENGTH: 7 amino acids
       ( B ) TYPE: amino acid
       ( C ) STRANDEDNESS:
       ( D ) TOPOLOGY: linear ( x i ) SEQUENCE DESCRIPTION: SEQ ID NO:14:

Phe Tyr Leu Lys Arg Lys Arg
1               5

( 2 ) INFORMATION FOR SEQ ID NO:15:

( i ) SEQUENCE CHARACTERISTICS:
       ( A ) LENGTH: 21 amino acids
       ( B ) TYPE: amino acid
       ( C ) STRANDEDNESS:
       ( D ) TOPOLOGY: linear ( x i ) SEQUENCE DESCRIPTION: SEQ ID NO:15:

Gly Pro Lys Glu Pro Phe Arg Asp Tyr Val Asp Arg Phe Tyr Leu Lys
1               5                      10                      15

Arg Lys Arg Ile His
                20

( 2 ) INFORMATION FOR SEQ ID NO:16:

( i ) SEQUENCE CHARACTERISTICS:
       ( A ) LENGTH: 4 amino acids
       ( B ) TYPE: amino acid
       ( C ) STRANDEDNESS:
       ( D ) TOPOLOGY: linear ( x i ) SEQUENCE DESCRIPTION: SEQ ID NO:16:

Ile Gly Pro Gly
1

( 2 ) INFORMATION FOR SEQ ID NO:17:

( i ) SEQUENCE CHARACTERISTICS:
( A ) LENGTH: 14 amino acids
( B ) TYPE: amino acid
( C ) STRANDEDNESS:
( D ) TOPOLOGY: linear ( x i ) SEQUENCE DESCRIPTION: SEQ ID NO:17:

Gly Pro Lys Glu Pro Phe Arg Asp Tyr Val Asp Arg Phe Tyr
1               5                       10

( 2 ) INFORMATION FOR SEQ ID NO:18:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:18:

Gly Pro Gly Ile
1

( 2 ) INFORMATION FOR SEQ ID NO:19:

( i ) SEQUENCE CHARACTERISTICS:
( A ) LENGTH: 7 amino acids
( B ) TYPE: amino acid
( C ) STRANDEDNESS:
( D ) TOPOLOGY: linear ( x i ) SEQUENCE DESCRIPTION: SEQ ID NO:19:

Phe Ala Arg Gly Pro Gly Ile
1               5

( 2 ) INFORMATION FOR SEQ ID NO:20:

( i ) SEQUENCE CHARACTERISTICS:
( A ) LENGTH: 12 amino acids
( B ) TYPE: amino acid
( C ) STRANDEDNESS:
( D ) TOPOLOGY: linear ( x i ) SEQUENCE DESCRIPTION: SEQ ID NO:20:

Phe Ala Arg Gly Pro Gly Ile His Ile Arg Lys Arg
1               5                       10

( 2 ) INFORMATION FOR SEQ ID NO:21:

( i ) SEQUENCE CHARACTERISTICS:
( A ) LENGTH: 14 amino acids
( B ) TYPE: amino acid
( C ) STRANDEDNESS:
( D ) TOPOLOGY: linear ( x i ) SEQUENCE DESCRIPTION: SEQ ID NO:21:

Phe Ala Arg Gly Pro Gly Ile His Ile Arg Lys Arg Lys Leu
1               5                       10

( 2 ) INFORMATION FOR SEQ ID NO:22:

( i ) SEQUENCE CHARACTERISTICS:
( A ) LENGTH: 4 amino acids (B) TYPE: amino acid
(C) STRANDEDNESS:
(D) TOPOLOGY: linear (xi) SEQUENCE DESCRIPTION: SEQ ID NO:22:

Arg Gly Pro Gly
1

(2) INFORMATION FOR SEQ ID NO:23:

(i) SEQUENCE CHARACTERISTICS:
(A) LENGTH: 4 amino acids
(B) TYPE: amino acid
(C) STRANDEDNESS:
(D) TOPOLOGY: linear (xi) SEQUENCE DESCRIPTION: SEQ ID NO:23:

Gly Pro Gly Ser
1

(2) INFORMATION FOR SEQ ID NO:24:

(i) SEQUENCE CHARACTERISTICS:
(A) LENGTH: 15 amino acids
(B) TYPE: amino acid
(C) STRANDEDNESS:
(D) TOPOLOGY: linear (xi) SEQUENCE DESCRIPTION: SEQ ID NO:24:

Ser Gly Pro Leu Lys Ala Glu Ile Ala Gln Arg Leu Glu Asp Val
1               5                   10                  15

(2) INFORMATION FOR SEQ ID NO:25:

(i) SEQUENCE CHARACTERISTICS:
(A) LENGTH: 9 amino acids
(B) TYPE: amino acid
(C) STRANDEDNESS:
(D) TOPOLOGY: linear (xi) SEQUENCE DESCRIPTION: SEQ ID NO:25:

Cys Thr Glu Leu Lys Leu Ser Asp Tyr
1               5

(2) INFORMATION FOR SEQ ID NO:26:

(i) SEQUENCE CHARACTERISTICS:
(A) LENGTH: 9 amino acids
(B) TYPE: amino acid
(C) STRANDEDNESS:
(D) TOPOLOGY: linear (xi) SEQUENCE DESCRIPTION: SEQ ID NO:26:

Val Ser Asp Gly Gly Pro Asn Leu Tyr
1               5

(2) INFORMATION FOR SEQ ID NO:27:

(i) SEQUENCE CHARACTERISTICS:
(A) LENGTH: 9 amino acids
(B) TYPE: amino acid
(C) STRANDEDNESS:
(D) TOPOLOGY: linear (xi) SEQUENCE DESCRIPTION: SEQ ID NO:27:

Ile Leu Arg Gly Ser Val Ala His Lys
1               5

PEPTIDE VACCINES AND METHODS RELATING THERETO

TECHNICAL FIELD

This invention relates generally to peptide vaccines incorporating a conformationally constrained reverse-turn mimetic capable of binding to a B cell, and a T cell stimulatory peptide covalently joined to the conformationally constrained reverse-turn mimetic by a cleavable linker.

BACKGROUND OF THE INVENTION

An effective vaccine is capable of generating a long-lasting immunity while being relatively harmless to the recipient. Attenuated organisms and purified antigens from organisms have traditionally been used as vaccines. However, such agents often produce deleterious side effects or fail to protect against subsequent challenges. Because of the inherent difficulties in growing pathogenic organisms and producing effective vaccines therefrom, many viral, bacterial and parasitic diseases have no corresponding vaccine. More recently, a new strategy of vaccine preparation has been explored. Specifically, short peptides, corresponding to regions of immunogenic epitopes of proteins derived from pathogens, have been used as vaccines in animal models. Such peptide vaccines offer several advantages over more traditional vaccines, including simplified preparation, increased safety and a directed immune response to a particular portion (i.e., an antigenic determinant) of a pathogen.

A major difficulty with the use of a peptide as a vaccine is that, in order to provoke a protective antibody response, the peptide must assume the same conformational shape as the antigenic determinant of the native pathogenic protein. The shape of the antigenic determinant is dictated by the primary amino acid sequence of the protein in the immediate region of the antigenic determinant, as well as by the amino acid sequence of regions close in three-dimensional space (although not necessarily close in linear space). While there may be some flexibility to the shape of the antigenic determinate, flexibility is limited. Short peptides are generally disordered structures and few, if any, antibodies raised to a disordered structure are likely to bind the corresponding antigenic determinant of the pathogen's native peptide sequence. Indeed, many anti-peptide antibodies do not bind native protein (see, e.g., Leonetti et al., *J. Immunol.* 145:4214–4221, 1990; Henrickson et al., *Vaccine* 9:243–249, 1991; Spangler, *J. Immunol.* 146:1591–1595, 1991). Such a pattern of response is not universal, however, and some anti-peptide antibodies do bind to the native protein, although often with low affinity and low titres (i.e., only a small percentage of the antibodies are made against the proper shape) (see, e.g., Conlan et al., *Mol. Microbiol.* 3:311–318, 1989; Palker et al., *J. Immunol.* 142:3612–3619, 1989; Su and Caldwell, *J. Exp. Med.* 175:227–235, 1992). The above results have often been referred to as the "disorder-order paradox", and models proposed to explain this paradox predict that peptides "shaped" into the particular three-dimensional structure of an antigenic determinant should increase the effectiveness of a peptide vaccine.

Various approaches have been followed in an attempt to shape peptides to mimic the native conformation of an antigenic determinant. For example, longer peptides, dimer peptides with an introduced bend, and cyclic peptides have all been tested with varying degrees of success. In particular, residues 140 to 146 in the hemagglutinin of influenza virus forms a loop in the native molecule and is one of the major antigenic sites. Immunization with this loop region, cyclized by a disulfide bridge, elicited antibodies that only weakly cross-reacted with influenza virus (Schulze-Gahmen et al., *Eur. J. Biochem.* 159:283–289, 1986). In contrast, immunization with a peptide derived from the same loop region, but cyclized by an amide bond, successfully elicited protective antibodies in some animals (Muller et al., *Vaccine* 8:308–314, 1990). While such results are promising, they nevertheless illustrate that cyclic peptides were not entirely accurate conformational representations of the native protein structure. Rather, peptides cyclized with disulfide bridges or amide linkages are still relatively flexible and, although they possess a smaller subset of conformations than linear peptides, do not necessarily assume the native conformation of the antigenic site.

More recent attempts to shape peptides have focused on a principal antigenic determinant of the AIDS virus—that is, the third hypervariable domain (known as the "$V_3$ loop") of the viral gp120 envelope glycoprotein of human immunodeficiency virus type 1 ("HIV-1"). While this determinant is believed to assume a beta-turn configuration, cyclized decapeptides from this region (i.e., decapeptides synthesized and then cyclized with an amide closure) were found to assume a beta-turn less than half the time (see, Tolman et al., *Int. J. Peptide Protein Res.* 41:455–466, 1993).

Other studies have similarly recognized the potential benefits of using peptides with introduced conformation as vaccines (see, e.g., Sia et al., PCT Application No. PCT/CA/00146, published Nov. 15, 1990 as WO 90/13564; Satterthwait et al., *Vaccine* 6:99, 1988; Leonetti et al., *J. Immunol.* 145:4214, 1990; Kaumaya et al., *J. Biol Chem.* 267:6338, 1992). However, these studies also illustrate a major limitation to existing techniques. Specifically, constraints introduced into peptides do not necessarily yield molecules having the ability to assume the native conformation of the corresponding antigenic determinant.

A further difficulty with the use of peptides as vaccines is that, in most instances, peptides alone are not good immunogens. It is a well known phenomenon that most immune responses to peptide antigens are T cell-dependent. Accordingly, "carrier" molecules have been attached to peptide antigens that bind, for example, to B cell surface immunoglobulin in order to generate a high affinity, IgG response. In other words, nonresponsiveness to peptide antigens may sometimes be overcome by attaching another peptide that induces helper T cell activity (see, e.g., Francis et al., *Nature* 330:168–170, 1987; Good et al., *Science* 235:1059–1062, 1987).

In general, peptides which induce helper T cell activity are generated by B cells from enzymatic digestion of native proteins internalized by way of an antibody receptor. These T cell stimulating peptides are then presented on the surface of the B cell in association with class II major histocompatibility complex (MHC) molecules. In a similar fashion, peptides which induce cytotoxic T cell activity may be generated by accessory cells, including B cells. These peptides are presented on the cell surface of accessory cells in association with class I MHC molecules. As used herein, the term "T cell stimulatory peptide" means any peptide which activates or stimulates T cells, including (but not limited to) helper T cells and/or cytotoxic T cells.

Peptides represent a promising approach to the production and design of vaccines. However, the difficulties in making peptides that induce the desired immune response, including the difficulties inherent in making peptides which closely mimic the native structure of antigenic determinants, have hampered their success. Accordingly, there is a need in the art for peptides which function as vaccines, and which preferably include both a conformationally constrained peptide region that binds to B cells and a T cell stimulatory peptide region. There is a further need in the art for appropriate linkers for covalently attaching such regions, and which further provide a suitable processing site for subsequent cleavage and presentation of the T cell stimulatory peptide on the surface of the B cell. The present invention fulfills these needs and provides further related advantages.

SUMMARY OF INVENTION

Briefly stated, the present invention is directed to a peptide vaccine comprising three regions: a conformationally constrained reverse-turn mimetic, a T cell stimulatory peptide, and a cleavable linker moiety covalently joining the conformationally constrained reverse-turn mimetic and the T cell stimulatory peptide. In another embodiment, this invention is directed to a method for generating a protective immune response in a warm-blooded animal by administration of the peptide vaccine to the animal. In yet a further embodiment, methods are disclosed for the synthesis of the peptide vaccine of this invention.

The conformationally constrained reverse-turn mimetics of this invention are capable of binding to a B cell, and preferably mimic the three-dimensional structure of an antigenic determinant of a native pathogenic protein. In contrast, the T cell stimulatory peptide stimulates or activates T cell activity when expressed on the surface of a B cell. The peptide vaccines of this invention produce an immune response by their ability to bind to B cell surface Ig, resulting in the internalization of the peptide vaccine via the Ig receptor. The linkers of this invention serve as cleavage sites for B cell intracellular enzymes, thus permitting separation of the conformationally constrained reverse-turn mimetic from the T cell stimulatory peptide. In the case of T cell stimulating peptides which activate helper T cells, the T cell stimulatory peptide is then presented on the surface of the B cell in association with class II MHC molecules, thus inducing helper T cell activity and generating a protective, humoral immune response.

Other aspects of this invention will become apparent upon reference to the following detailed description.

DETAILED DESCRIPTION OF THE INVENTION

As mentioned above, this invention is generally directed to a peptide vaccine which is capable of generating an immune response in a warm-blooded animal. As used herein, a "peptide vaccine" is a compound comprising a conformationally constrained reverse-turn mimetic capable of binding to a B cell, a T cell stimulatory peptide, and a cleavable linker covalently joining the conformationally constrained reverse-turn mimetic to the T cell stimulatory peptide. This invention is also directed to a method of administrating the peptide vaccine to a warm-blooded animal to generate a protective immune response, and to methods for synthesizing the peptide vaccine.

In one embodiment, the peptide vaccine of this invention generates immunity in an animal by provoking a protective humoral antibody response following its administration to the animal. In other words, the Ig elicited by the B cells are directed against a neutralizing epitope of a pathogenic protein. Alternatively, the peptide vaccine may activate or stimulate cytotoxic T cells. Administration of the peptide vaccines of this invention may be accomplished by known techniques commonly employed for administration of existing vaccines, including (but not limited to) subcutaneous and intramuscular injection (see, Stevens et al., *Am. J. Reprod. Immunol.* 1:315–321, 1981: Babink, *Immunochemist of Viruses—The Basis of Serodiagnosis and Vaccines*, p. 189, Van Regenmortol and Neurath eds, Elsevier, Amsterdam, 1985; Brunell, *Immunochemist of Viruses—The Basis of Serodiagnosis and Vaccines*, p. 171, Van Regenmortol and Neurath editors, Elsevier, Amsterdam, 1985) (incoporated by reference herein). The peptide vaccine is administered in an mount sufficient to provoke a protective immune response, and may be supplemented with subsequent "boosters" as needed.

As used herein, a "conformationally constrained reverse-turn mimetic" is a compound capable of binding to a B cell by interaction with an antibody receptor on the surface of the B cell. The structure of the conformationally constrained reverse-turn mimetic is preferably derived from an antigenic determinant of a native protein (such as a pathogenic protein), and mimics the three-dimensional structure thereof. Thus, antibodies raised to the conformationally constrained reverse-turn mimetic will bind to the corresponding antigenic determinant of the native protein.

The conformationally constrained reverse-turn mimetics of this invention encompass compounds of related structures, including mimetics of beta-turns, gamma-turns and beta-bulges. In general, beta-turns are reversals in the direction of a polypeptide chain wherein the oxygen of the CO group of amino acid n is hydrogen bonded to the hydrogen of the NH group of amino acid n+3. Similarly, gamma-turns and beta-bulges are reversals in a polypeptide chain where the oxygen of the CO group of amino acid n is hydrogen bonded to the hydrogen of the NH group of amino acid n+2 and n+4, respectively. The conformationally constrained reverse-turns of this invention "mimic" the three-dimensional structure of beta-turns, gamma-turns and beta-bulges, and thus serve as surrogates for such reverse-turn structures present in naturally-occuring proteins and/or peptides.

More specifically, a conformationally constrained beta-turn mimetic of this invention has the following structure I or II:

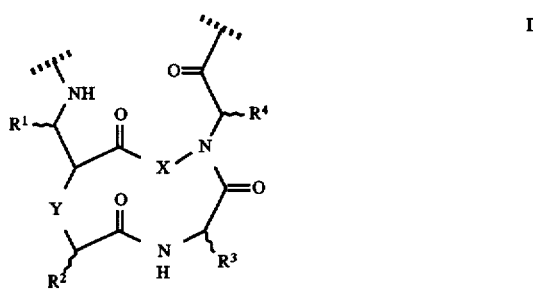

I

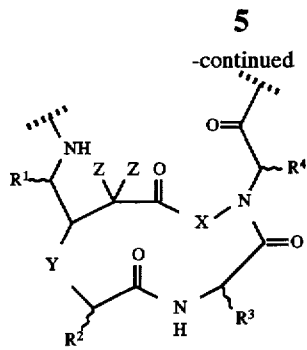

wherein $R^1$, $R^2$, $R^3$ and $R^4$ are amino acid side chain moieties or derivatives thereof, X is selected from the chemical moieties identified in Table 1, Y is selected from —CH$_2$—, —N(Z)—, —O— and —S—, and Z is —H or —CH$_3$.

A conformationally constrained gamma-turn mimetic of this invention has the following structure III or IV:

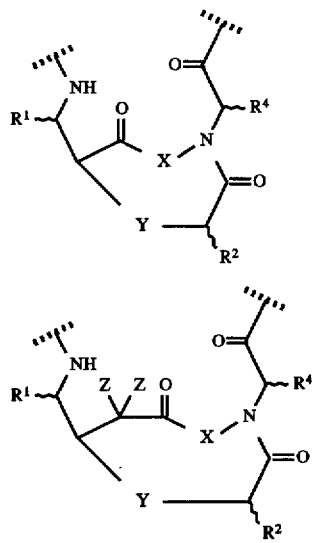

wherein $R^1$, $R^2$ and $R^4$ are amino acid side chain moieties or derivatives thereof, X is selected from the chemical moieties identified in Table 1, Y is selected from —CH$_2$—, —N(Z)—, —O— and —S—, and Z is —H or —CH$_3$.

A conformationally constrained beta-bulge mimetic of this invention has the following structure V or VI:

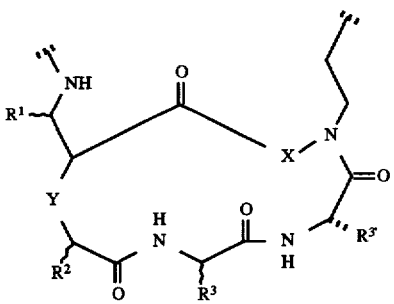

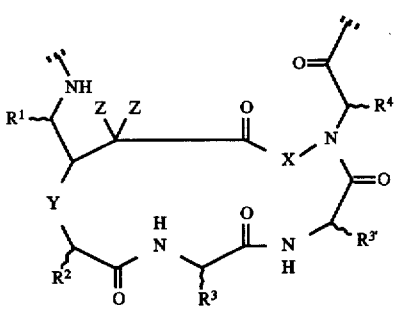

wherein $R^1$, $R^2$, $R^3$, $R^{3'}$ and $R^4$ are amino acid side chain moieties or derivatives thereof, X is selected from the chemical moieties identified in Table 1, Y is selected from —CH$_2$—, —N(Z)—, —O—, and —S—, and Z is —H or —CH$_3$.

TABLE 1

"X" Moieties of Structures I through VI

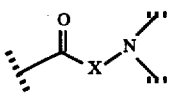

where X =

| | |
|---|---|
| —NH— | —NHC(Z)$_2$CH$_2$— |
| —NHC(Z)$_2$CH$_2$CH$_2$CH$_2$— | —NHC(Z)$_2$CH═CHCH$_2$— |
| —NH(CH$_2$)$_n$— | —NHC(Z)$_2$(CH$_2$)$_n$— |
| —NH(CH$_2$)$_n$CH═CH— | —NH(CH$_2$)$_n$C≡C— |
| —NHC(Z)$_2$(CH$_2$)$_n$NH— | —NHNHC(Z)$_2$(CH$_2$)$_n$— |
| —NHC(Z)$_2$CH═CH(CH$_2$)$_n$— | —NHC(Z)$_2$C≡C(CH$_2$)$_n$— |
| —NHC(Z)$_2$CH═C(Z)(CH$_2$)$_n$— | —NHC(Z)$_2$CH═CH(CH$_2$)$_n$NH— |
| —NHNHC(Z)$_2$CH═CH(CH$_2$)$_n$— | —NHC(Z)$_2$(CH$_2$)$_n$CH═N— |
| —NHC(Z)$_2$(CH$_2$)$_n$CH═C═N— | —NHC(Z)$_2$(CH$_2$)$_n$CH═CHCH═N— |
| —NHC(Z)$_2$(CH$_2$)$_n$C≡CCH═N— | —NHC(Z)$_2$(CH$_2$)$_n$CONH— |

TABLE 1-continued

"X" Moieties of Structures I through VI

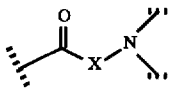

where X =

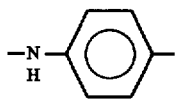  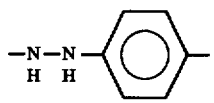

(where n = 1–4 and Z = H or CH$_3$)

---

As used herein, the designation "∼R" indicates that the amino acid side chain moiety (or derivative thereof) may lie either above or below the plane of the page. In the case of naturally occuring amino acids (i.e., "L-amino acids"), the R amino acid side chain moieties would lie below the plane of the page in structures I through VI above (i.e., " ⋯ııR"). However, if one or more D-amino acids were employed, the corresponding R amino acid side chain moiety would lie above the plane of the page in the above structures (i.e., " R"). In a preferred embodiment, L-amino acids are employed to more closely mimic the structure of native protein. The designation "ıııı" indicates the remainder of the molecule. In other words, additional chemical moieties are covalently attached to the terminal carbonyl and amine groups of structures I through VI above. This aspect of the invention is addressed in greater detail below. Moreover, it should be understood that the chiral carbon immediately adjacent to the carbon atom having the amino acid side chain moiety R$^1$ of structures I through VI may be in either the α- or β-position. In other words, this carbon atom may have either of the following structures:

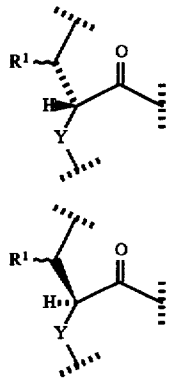

As used herein, the term "an amino acid side chain moiety" represents any amino acid side chain moiety present in naturally occurring proteins, including (but not limited to) the naturally occurring amino acid side chain moieties identified in Table 2. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine.

TABLE 2

Amino Acid Side Chain Moieties

| Amino Acid Side Chain Moiety | Amino Acid |
|---|---|
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3$$^+$ | Lysine |
| —(CH$_2$)$_3$NHC(NH$_2$)NH$_2$$^+$ | Arginine |
| —CH$_2$-(imidazole) | Histidine |
| —CH$_2$COO— | Aspartic acid |
| —CH$_2$CH$_2$COO | Glutamic acid |
| —CH$_2$CONH$_2$ | Asparagine |
| —CH$_2$CH$_2$CONH$_2$ | Glutamine |
| —CH$_2$-(phenyl) | Phenylalanine |
| —CH$_2$-(phenyl)-OH | Tyrosine |
| —CH$_2$-(indole) | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| —HN-(pyrrolidine) | Proline |

TABLE 2-continued

Amino Acid Side Chain Moieties

| Amino Acid Side Chain Moiety | Amino Acid |
|---|---|
| 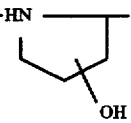 | Hydroxyproline |

When the amino acid side chain moiety of structures I through VI is proline, the five-membered pyrrolidine ring may be a component of the conformationally constrained reverse-turn mimetic. In other words, proline may be present at any location within the conformationally constrained reverse-turn mimetic in place of one or more "—NH—CH(R)—" moieties. For example, inclusion of proline in structures I through VI above at the "—Y—CH(R$^2$)—" position (where Y=N) yields the following structures I(a) through VI(a):

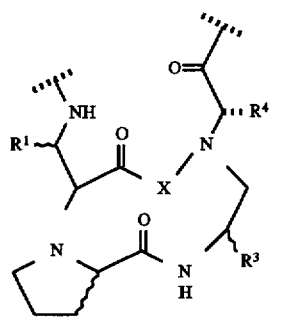
I(a)

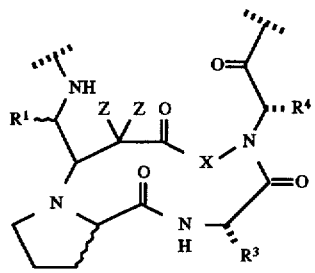
II(a)

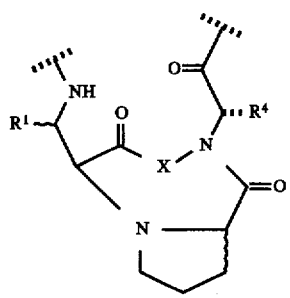
III(a)

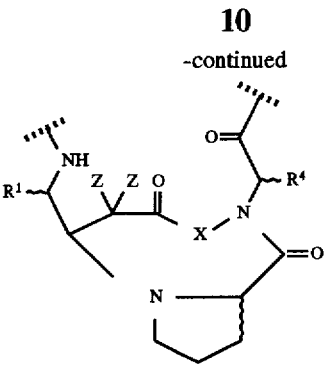
IV(a)

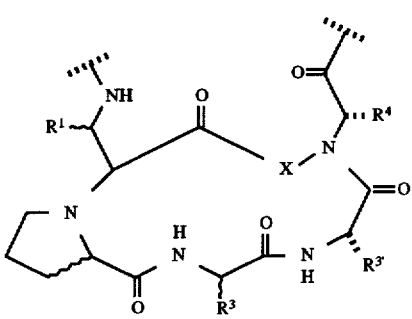
V(a)

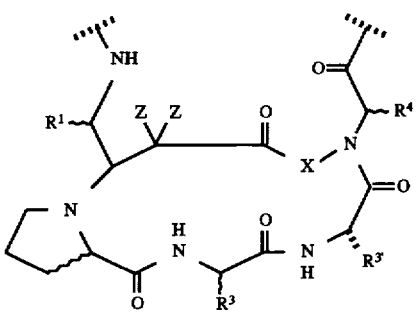
VI(a)

where R$^1$, R$^3$, R$^{3'}$, R$^4$, X and Z are as identified above with regard to structures I through VI.

Alternatively, structures I and II may be modified by inclusion of proline within the conformationally constrained reverse-turn mimetic at the "—NH—CH(R$^3$)—" position, yielding structures I(b) and II(b) below:

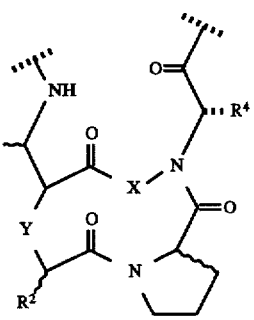
I(b)

-continued

II(b)

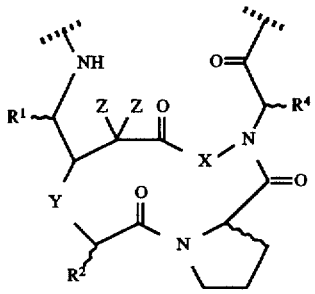

Similarly, structures V and VI may be modified by inclusion of proline within the conformationally constrained reverse-turn mimetic at the "—NH—CH($R^3$)—" or "—NH—CH($R^{3'}$)—" positions, yielding structures V(b), VI(b), V(c) and VI(c):

V(b)

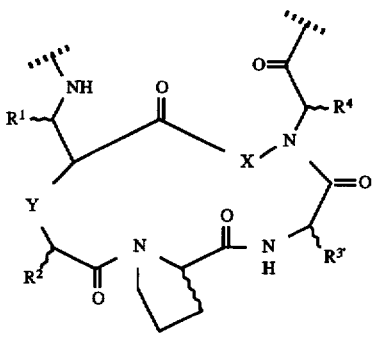

VI(b)

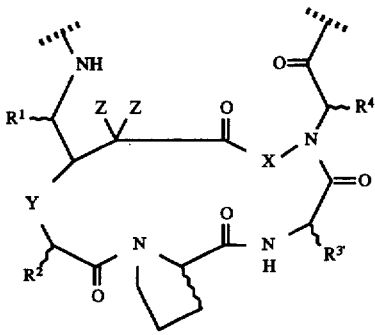

V(c)

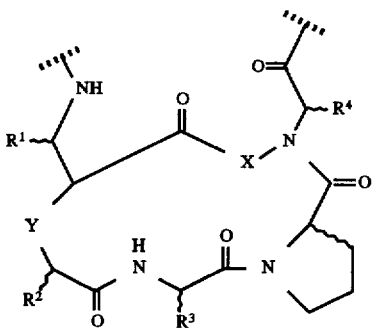

-continued

VI(c)

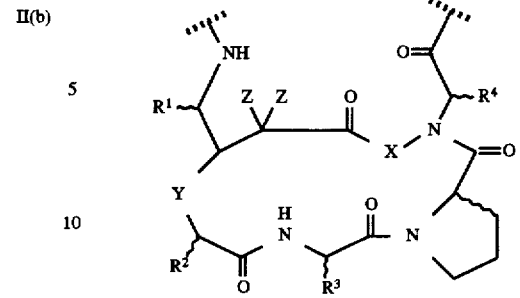

where $R^1$, $R^2$, $R^3$, $R^{3'}$, $R^4$, X, Y and Z are as identified above with regard to structures I through VI.

Accordingly, general structures I through VI above include structures I(a), II(a), III(a), IV(a), V(a), VI(a), I(b), II(b), V(b), VI(b), V(c) and VI(c) as representative examples where the amino acid side chain moiety is proline (or a derivative thereof).

The conformationally constrained reverse-turn mimetics of the present invention are made by utilizing appropriate starting component molecules (hereinafter referred to as "component pieces"). In short, first, second and third component pieces are combined (in various combinations) and then cyclized to yield the conformationally constrained reverse-turn mimetics of this invention.

Within the context of this invention, a "first component piece" has the following structure 1:

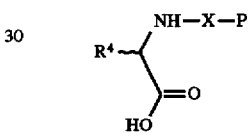
1 wherein $R^4$ is an amino acid side chain moiety or derivative thereof, X is selected from the chemical moieties identified in Table 1, and P is a protective group suitable for use in peptide synthesis.

A "second component piece" of this invention is selected from the following structures 2(a), 2(b) and 2(c):

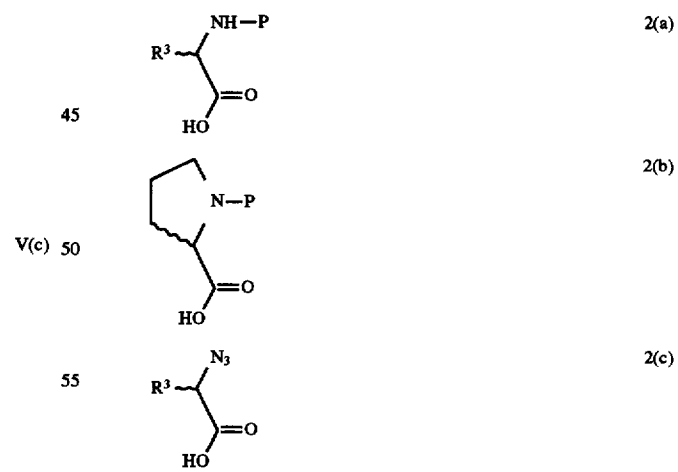

wherein $R^3$ is an amino acid side chain moiety or derivative thereof, and P is a protective group suitable for use in peptide synthesis.

A "third component piece" of this invention is selected from the following structures 3(a), 3(b) and 3(c):

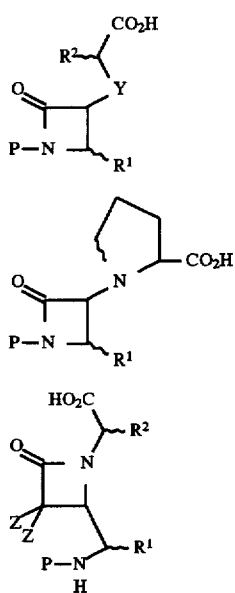

3(a)

3(b)

3(c)

where $R^1$ and $R^2$ are amino acid side chain moieties or derivatives thereof, Y is —$CH_2$—, —NZ—, —O— or —S—, Z is H or methyl, and P is a protective group suitable for use in peptide synthesis. Thus, when Y of structure 3(a) is —$CH_2$—, —NZ—, —O— or —S—, the following third modular component pieces 3(a1), 3(a2), 3(a3) and 3(a4), respectively, are obtained:

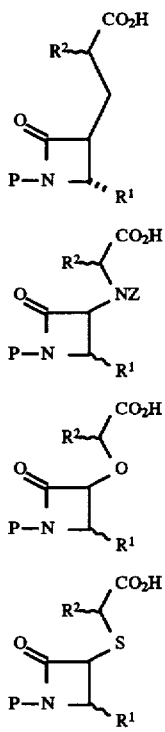

3(a1)

3(a2)

3(a3)

3(a4)

More specifically, conformationally constrained beta-turn mimetics of this invention (see structures I and II above) are synthesized by reacting a first component piece with a second component piece to yield a combined first-second intermediate, followed by reacting the first-second intermediate with a third component piece to yield a combined first-second-third intermediate, and then cyclizing the resulting first-second-third intermediate to yield the conformationally constrained beta-turn mimetic. Conformationally constrained gamma-turn mimetics (see structures III and IV above) are synthesized in the same manner, except that the second component piece is omitted (i.e., a first-third intermediate is cyclized). Similarly, conformationally constrained beta-bulges (see structures V and VI above) are synthesized by use of two second component pieces (i.e., a first-second-second-third intermediate is cyclized).

For example, the general synthesis of a conformationally constrained beta-turn mimetic having structure 4 below may be synthesized by the following technique. A first modular component piece 1 is combined with a second modular component piece 2(a) to yield a first-second intermediate 5 as illustrated below (it should be recognized that following reaction scheme is presented for illustration purposes, and that the carboxylic acid moiety of structure 1 should be suitably protected by, for example, esterification, by formation of an amide bond, or by attachment to a solid support):

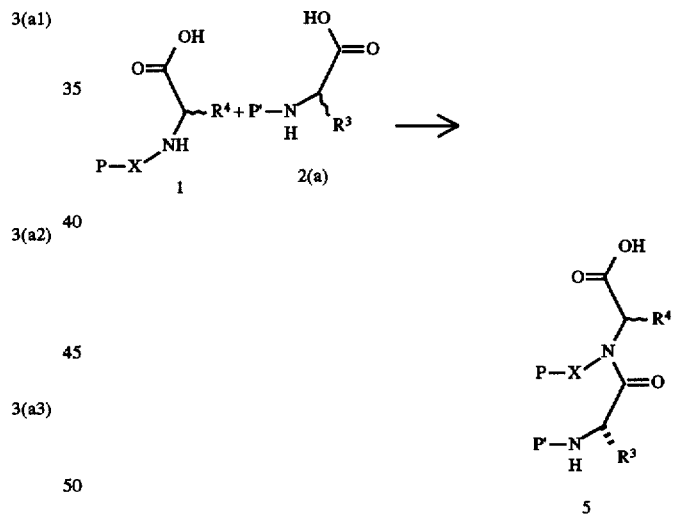

A third modular component piece 3(a1) is then combined with the first-second intermediate 5 to give a pre-cyclized beta-turn mimetic 6, which in turn is cyclized to yield the beta-turn mimetic of structure 4:

All conformationally constrained reverse-turn mimetics of this invention may be synthesized by appropriate choice of the various component pieces by the general procedure outlined above. For example, R group variations to structures I through VI may be made by use of appropriate first, second and third component pieces possessing the desired R group. Similarly, conformationally constrained gamma-turn mimetics may be synthesized by linking a first component piece with a third component piece (omitting the second component piece), followed by cyclization. Alternatively, a first component piece may be combined with a second component piece, followed by combination with yet another second component piece to yield a first-second-second intermediate. This intermediate may then be combined with a third component piece and cyclized to yield the corresponding conformationally constrained beta-bulge mimetic. Additional disclosure directed to the synthesis of the conformationally constrained reverse-turn mimetics of this invention is set forth in Examples 1-3 below.

For use as vaccines, the conformationally constrained reverse-turn mimetics of this invention mimic the three-dimensional structure of an antigenic region of a native protein, including both pathogenic and non-pathogenic proteins. An example of a non-pathogenic protein is the mammalian zona pellucida which surrounds growing oocytes and ovulated eggs, and thus may serve as an immunogen for a contraceptive vaccine (Millar et al., Science 246:935, 1989). Due to their biological importance, many antigenic sites of native proteins have been identified and their three-dimensional conformation determined by, for example, X-ray crystallography and/or molecular modeling. For such antigenic regions, a conformationally constrained reverse-turn mimetic of this invention can be readily designed. The following disclosure illustrates the design of conformationally constrained reverse-turn mimetics for major neutralizing determinants of two medically important pathogens, HIV and human influenza virus.

With regard to HIV, the $V_3$ loop of the gp120 envelope protein is a principal neutralizing determinant, and the precise conformation of the antigenic region of the $V_3$ loop is critical to eliciting neutralizing antibodies. The peptide sequence of the $V_3$ loop encompasses from amino acids 306 to 317 and has a consensus sequence RKRIHIGPGRAF (SEQ ID NO.1), with the region glycyl-prolyl-glycyl-argyl (GPGR) (SEQ ID NO.2) being a conserved sequence among different strains of HIV. It is believed that conservation among different HIV-1 isolates of the GPGR region is due to the necessity of maintaining an essential beta-turn in the crown of the $V_3$ loop. It is also believed that the binding of gp120 to CD4 at a site remote from the $V_3$ loop induces a conformational shift in the $V_3$ loop. This shift results in a frame shift of a type II beta-turn incorporating a proline in the i+1 position to a type VI beta-turn with a proline in the i+2 site (Johnson et al., FEBS Letters 337:4–8, 1994). Such a CD4-induced frame shift would provide a mechanism for presentation of the $V_3$ loop as a competent "trypsin-like" substrate to a cellular protease for activation of subsequent membrane fusion. The following two conformations (designated A and B) of the $V_3$ loop have been determined by molecular modeling (one conformation having Pro313 in the i+1 position of a type II reverse-turn, and the other having Pro313 in the i+2 position of a type VI reverse-turn, respectively):

A
(proline at i + 1)

B
(proline at i + 2)

The synthesis of conformationally constrained reverse-turns which mimic the three-dimensional structure of the above V₃ loop conformations are presented in Example 4 below.

Similarly, the three-dimensional conformation of amino acid residues 140 to 146 (i.e., KRGPGSG) (SEQ ID NO.3) of the hemagglutinin surface protein of influenzae virus has been shown by X-ray crystallography to adopt the following loop structure (Wilson et al., Nature 289:368–373, 1981):

This loop contains a major antigenic site of the virus, and antibodies to this region neutralize viral infection. Accordingly, conformationally constrained reverse-turns of this invention may be synthesized to mimic the three-dimensional loop structure of this region (see Example 5 below).

While conformationally constrained reverse-turn mimetics of this invention can be readily synthesized to mimic a known antigenic determinant region, synthesis can also be accomplished when the three-dimensional structure of the antigenic determinant region is not known. For example, an existing monoclonal antibody to the $C_4$ region of gp120 (e.g., MAb 5C2E5) interferes with binding of the envelope to CD4 on T cells (Lasky et al., Cell 50:975–985, 1987). The epitope detected by this antibody encompasses amino acids 406 to 415 (i.e., QIINMWQKVG) (SEQ ID No.4). Thus, conformationally constrained reverse-turn mimetics to $C_4$ may be identified by predicting the conformation of this region based on the observed homology between gp120 and the constant region of immunoglobulins (the three-dimensional structure of immunoglobulins having been established by X-ray crystallography). For example, conformationally constrained reverse-turn mimetics may be synthesized containing different "X" moieties (see structures I through VI) to approximately conform to the deduced structure. Conformationally constrained reverse-turn mimetics may then be identified by screening their ability to bind to MAb 5C2E5 or CD4 in a standard ELISA assay. In situations where there are no known neutralizing antibodies, antibodies to candidate conformationally constrained reverse-turn mimetics can be raised and tested for pathogen neutralization.

In some instances, epitopes are discontinuous—that is, the three-dimensional region of the antigenic determinant includes contributions from amino acids from discrete parts of the polypeptide chain. For example, some neutralizing antibodies to HIV recognize the combination of $V_3$ and $C_4$ domains (Thali et al., *J. Acquired Immune Defic. Syndr.* 6:591, 1992; Thali et al., *J. Virol.* 66:5635, 1992), and these domains are close together in three-dimensional space (Wyatt et al., *J. Virol.* 66:6997, 1992). In such instances, two conformationally-constrained reverse-turn mimetics of this invention may by joined with the use of a suitable spacer moiety to mimic the discontinuous epitopes. For example, the following molecule may serve as a spacer moiety of this invention:

(reverse-turn mimetic)—NH—C(=O)—[naphthalene]—C(=O)—NH—(reverse-turn mimetic)

In addition to mimicking the three-dimensional structure of an antigenic region of a native protein, the conformationally constrained reverse-turn mimetics of this invention are also capable of binding to B cells and provoking a protective immune response. To date, numerous B cell recognition sites have been reported and are summarized by David R. Milich in Table II, "Enumeration of B Cell Sites", of *Advances in Immunology* 45:240–250, 1989 (hereby incorporated by reference in its entirety).

B cell proliferation requires T cell stimulation to elicit an immune response. Accordingly, the peptide vaccines of this invention further comprise a T cell stimulatory peptide covalently attached to the conformationally constrained reverse-turn mimetic. Peptides capable of eliciting a helper T cell response generally range from 10–20 amino acids, and more preferably from 12–15 amino acids in length. Suitable T cell stimulatory peptides of this invention are peptides which induce T cell activity when presented on the surface of a B cell, including peptides which activate or stimulate helper T cell activity when presented in association with class II MHC molecules, as well peptides which activate or stimulate cytotoxic T cells when presented in association with class I MHC molecules. Suitable T cell stimulatory peptides include, but are not limited to, peptides from gp120 and p24E proteins of HIV which have been identified and shown to be stimulatory in mice (Cease et al., *Proc. Natl. Acad. Sci. USA* 84:4249, 1987; PCT Patent Applicant Publication No. WO 90/13564). In particular, the T cell stimulatory peptides derived from gp120 and p24E correspond to the sequences KQIINMWQEVGKAMYA (SEQ ID NO.5) and GPKEPFRDYVDRFYK (SEQ ID NO. 6), respectively, and may serve as suitable T cell stimulatory peptides for peptide vaccines directed to HIV.

Suitable T cell stimulatory peptides for other vaccines can be identified in a similar fashion, and various algorithms may be used to predict such candidate peptides. In addition, suitable assay techniques may be employed to identify T cell stimulatory peptides of this invention. For example, the in vitro assay measuring proliferation of lymph node T cells disclosed by Leonetti et al. (*J. Immunol.* 145:4214–4221, 1990) may be used to identify T cell stimulatory peptides of this invention. In this assay, mice are immunized subcutaneously at the base of the tail with the candidate peptides in complete Freund's adjuvant or equivalent adjuvant. After eight days, the draining lymph nodes are removed, and a single cell suspension is made. The lymph node cells are then cultured in triplicate with serial dilutions of candidate peptides, or medium alone, for 24 hours. The presence of IL-2 in the culture supernatants is evaluated by determining the proliferation of an IL-2 dependent cell line, such as CTL. CTL cells are incubated with an aliquot of culture supernatant for 24 hours and then pulsed with [$^3$H]TdR, and the mount of incorporated radioactivity determined.

Representative embodiments of suitable T cell stimulatory peptides (amino-terminal to carbonyl-terminal) are listed in Table 3 below, along with corresponding references (all of which are hereby incorporated by reference in their entirety). Further T cell stimulatory peptides include known peptides which correspond to the T cell recognition sites summarized by David R. Milich in Table I, "Enumeration of T Cell Sites", of *Advances in Immunology* 45:204–209, 1989 (hereby incorporated by reference in its entirety). In addition, suitable T cell stimulating peptides may be identified by known techniques, including acid elution and sequencing (Rudensky, *Nature* 353:622, 1991) and mass spectrometry (Hunt et al., *Science* 256:18–17, 1992). Phage display techniques may also be employed to define both anchor and promiscuous residues according to MHC alleles (see, e.g., Hammer et al., *Cell* 74:197–203, 1993)(see also, Kilgus et al., *Proc. Natl. Acad. Sci. USA* 86:1629–1633, 1989; Rötzschke et al., *Nature* 348:252–254, 1990; Hunt et al., *Science* 255:1261–1263, 1992; Ferrari et al., *J. Clin. Invest.* 88:214–222, 1991). All of the above documents are incorporated herein by references in their entirety.

TABLE 3

T-Cell Stimulating Peptides

| Peptide Sequence | | Source | Reference |
|---|---|---|---|
| GPKEPFRDYVDRFYK | (SEQ ID NO. 6) | p24E | PCT Patent Application Publ. No. WO 90/13564 |
| GPKEPFRDYVDRFYK-TLRAEQASQEV | (SEQ ID NO. 7) | HIV1-p24 | PCT Patent Application Publ. No. WO 90/13564 |
| KQIINMWQEVGKAMYA, HEDIISLWNQSLK | (SEQ ID NO. 5) (SEQ ID NO. 8) | gp120 | Cease et at., Proc. Natl. Acad. Sci. USA 84:4249–4253, 1987 |
| YKKVWRDHRGTIIERGC | (SEQ ID NO. 9) | Neuro toxin from *Naja nigicolollis* venom | Leonetti et al., J. Immunol. 145:4214–4221, 1990 |
| AVYTRIMMNGGRLKR | (SEQ ID NO. 10) | Evelyn-Rokitnicki-Abelseth strain of | Dietzschold et al., J. Virology 64:3804–3809, 1990 |

TABLE 3-continued

T-Cell Stimulating Peptides

| Peptide Sequence | Source | Reference |
|---|---|---|
| KQIRDSITEEWS (SEQ ID NO. 11) | rabies virus Rodent malaria parasite, *Plasmodium berghei* | Tam et al., J. Exp. Med. 171:299–306, 1990 |

The conformationally-constrained reverse-turn mimetics and the T cell stimulatory peptides of this invention are covalently joined by a cleavable linker. As mentioned above, T cell stimulatory peptides presented by class II MHC molecules are generally generated by proteolytic degradation of an endocytosed protein, and such degradation generally occurs in a lysosomal compartment of a B cell. Alternatively, T cell stimulatory peptides presented by class I MHC molecules generally involve nuclear/cytosolic degredation by the proteasome (a large ATP-dependent proteolytic complex). Thus, any linker which is readily subject to proteolytic degredation in the lysosomal compartment of the B cell, or subject to nuclear/cytosolic degredation by the proteasome, may serve as a linker moiety within the context of this invention. Preferred linkers are amino acid sequences capable or prone to proteolytic breakdown.

One of the most abundant proteolytic enzymes in lysosomes is Cathepsin D. Thus, a preferred linker of this invention contains a recognition site (i.e., cleavage site) for Cathepsin D. The amino acid sequence pattern that is preferentially cleaved by cathepsin D from bovine spleen is presented below (see, van Noort et al., *J. Biol. Chem.* 24:14159–14164, 1989):

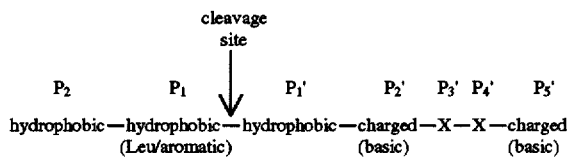

where $P_2$ through $P_5'$ represent amino acids, with cleavage by Cathepsin D occurring between the $P_1$ and $P_1'$ amino acids. Accordingly, any amino acid sequence satisfying the above functional parameters may be employed as a cleavable linker in this invention.

For example, a peptide vaccine of this invention directed to the $V_3$ loop of the gp120 envelope protein (i.e., a neutralizing determinant) may utilize conformationally constrained beta-turn mimetics to both loop conformations of amino acids 306 to 317 of gp120 (i.e., RKRIHIGPGRAF) (SEQ ID NO.1). For purposes of illustration, such conformationally constrained reverse-turn mimetics may be represented as the following sequences a and b:

In other words, sequence a represents conformationally constrained reverse-turn mimetics to the proline in the i+1 conformation (see structure A above), and sequence b represents the proline in the i+2 conformation (see structure B above). It should be understood that sequences a and b represents conformationally constrained beta-turn mimetics of varying ring size. By varying "X" of structures I and II, the ring size of the conformationally constrained beta-turn mimetic may be varied (for example, 10-, 12- and 14-membered rings may be produced). Accordingly, sequences a and b represent conformationally constrained beta-turn mimetics of varying three-dimensional conformations.

When a T cell stimulating peptide (such as p24E) is covalently attached to sequences a and b, the resulting sequences c and d are produced:

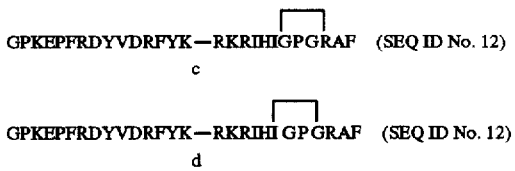

As mentioned above, a cleavable linker of this invention is located between the T cell stimulatory peptide and the conformationally constrained reverse-turn mimetic. For example, in the case of a linker cleavable by Cathepsin D, the terminal lysine (K) of the T cell stimulatory peptide of sequence c and d may be replaced with leucine-lysine (LK) to yield the following sequences e and f:

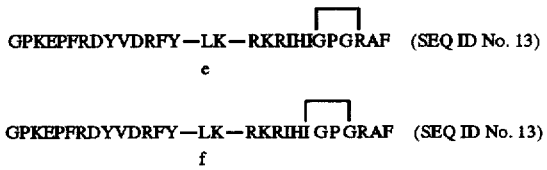

The phenylalanine-tyrosine-leucine-lysine-arginine-lysine-arginine sequence (FYLKRKR)(SEQ ID NO.14) may now serve as a cleavable linker between the T cell stimulatory peptide and the conformationally constrained reverse-turn mimetic, with cleavage by Cathepsin D occurring between tyrosine and leucine (i.e., between the $P_1$ and $P_1'$ amino acids).

Other cleavable linkers of this invention include, but are not limited to, the amino acid sequences which are cleavable by cathepsin B or by cathepsin E. Cathepsin B is a cystein proteinase which cleaves sequences having a basic amino acid (such as arginine or lysine) at the $P_2$ and $P_3$ positions, a small hydrophobic moiety at $P_1$, and an aromatic hydrophobic moiety at $P_1'$ and $P_4$ (see Matsueda et al., *The Chemical Society of Japan—Chemistry Letters* pp. 1857–1860, 1988; Matsunaga et al., *FEBS* 324:325–330, 1993). Similarly, cathepsin E is an endosomal aspartic proteinase present in both B and T cells, but not in peritoneal macrophages. The active cleft of this enzyme is capable of accommodating as many as nine residues, with a distinct preference for cleavage to occur between hydrophobic residues occupying the $P_1$-$P_1'$ sites (e.g., Bennett et al., *Eur. J. Immunol.* 22:1519–1524, 1992).

Synthesis of the peptide vaccines of the present invention may be accomplished using known peptide synthesis techniques, in combination with the first, second and third component pieces of this invention. More specifically, any amino acid sequence may be added to the N-terminal and/or C-terminal of the conformationally constrained reverse-turn mimetic. For example, to synthesize a peptide vaccine of sequence f above, the amino acid sequence FAR is sequentially synthesized on a solid support (such as PAM resin) by known techniques (see, e.g., John M. Stewart & Jamin D. Young, *Solid Phase Peptide Synthesis*, 1984, Pierce Chemical Comp., Rockford, Ill.):

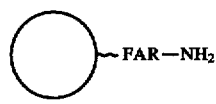

(It should be noted that such solid phase synthesis normally occurs from carbonyl to amino terminus, thus yielding the peptide vaccine of sequence f depicted above from amino to carbonyl terminus.) A first component piece is then added:

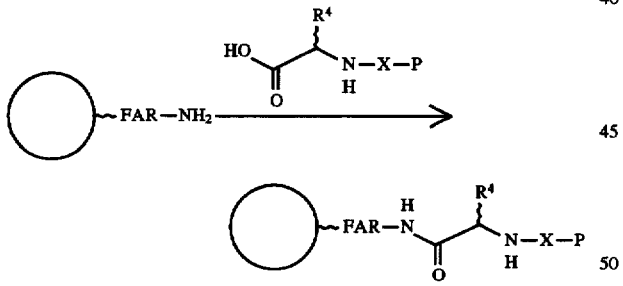

This is followed by addition of a second component piece:

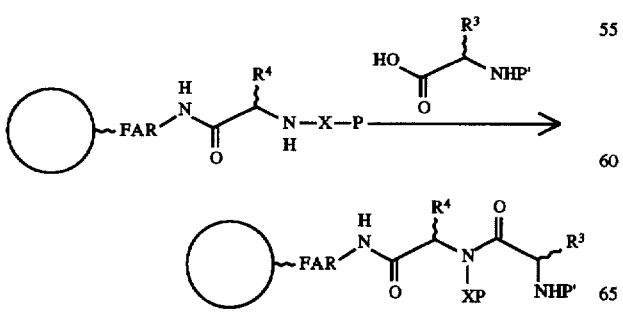

The terminal nitrogen is deprotected (i.e., removal of P'), and a third component piece added (where Y is —$CH_2$—, —NZ—, —O— or —S—):

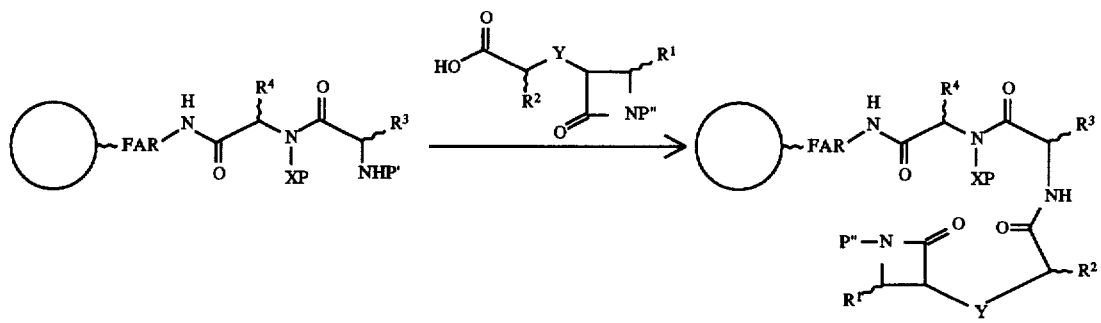

The P and P" protected nitrogens are then deprotected, and the first, second and third component pieces cyclized:

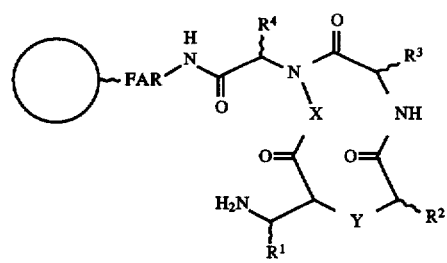

Amino acids (SEQ ID NO.15) are then added to the N-terminus of the conformationally constrained beta-turn mimetic by known synthesis techniques to yield:

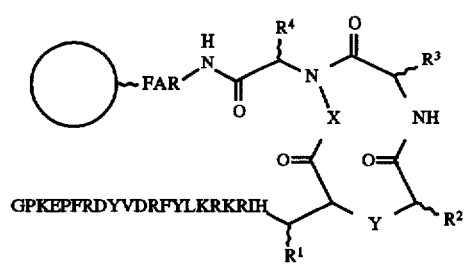

The resulting compound is then cleaved from the solid support to yield the peptide vaccine.

Since the above structure is a conformationally constrained reverse-turn mimic of structure f, and thus intended to mimic the IGPG-turn, (SEQ ID NO.16) the amino acid side chain moieties of isoleucine, glycine, proline and glycine would be utilized for $R^1$, $R^2$, $R^3$ and $R^4$, respectively, and Y would be —NH— or —$CH_2$— as illustrated below:

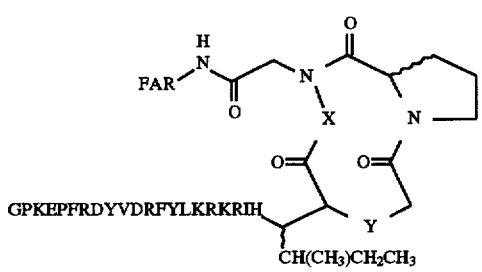

(In this example, the second component piece would correspond to structure 2(b) due to the presence of the proline amino acid side chain at R³.) Moreover, the three-dimensional structure of the conformationally constrained beta-turn mimetic may be controlled by appropriate choice of the "X" moiety. For example, 10-, 12- and 14-membered rings (e.g., corresponding to X=—NH—, —NHCH₂CH₂—, and —NH(CH₂)₄-respectively) may be synthesized. Other suitable "X" moieties of this invention are set forth in Table 1 above.

Alternatively, synthesis of peptide vaccines of this invention may be accomplished in solution, rather than on a solid support as disclosed above. Suitable techniques for synthesizing the conformationally constrained reverse-turn mimetics of this invention are disclosed in PCT application number PCT/US92/00916 filed Feb. 6, 1992 and published as WO92/138878 on Aug. 20, 1992, and PCT application number PCT/US93/07447 filed Aug. 6, 1993 and published as WO94/03494 on Feb. 17, 1994 (both of which references are incorporated herein by reference in their entirety).

In addition, a combination of both solution and solid phase synthesis techniques may be utilized to synthesize the peptide vaccines of this invention. For example, a solid support may be utilzed to synthesize the the linear peptide sequence up to the point that the conformationally constrained reverse-turn is added to the sequence. A suitable conformationally constrained reverse-turn mimetic which has been previously synthesized by solution synthesis techniques may then be added as the next "amino acid" to the solid phase synthesis (i.e., the conformationally constrained reverse-turn mimetic, which has both an N-terminus and a C-terminus, may be ulitized as the next amino acid to be added to the linear peptide). Upon incorporation of the conformationally constrained reverse-turn mimetic into the sequence, additional amino acids may then be added to complete the peptide vaccine bound to the solid support. Alternatively, the linear N-terminus and C-terminus protected peptide sequences may be synthesized on a solid support, removed from the support, and then coupled to the conformationally constrained reverse-turn mimetic in solution using known solution coupling techniques.

The effectiveness of the peptide vaccines of this invention may be tested by determining IgG antibody titers to the immunogen (i.e., the peptide vaccine), IgG antibody titers to the native protein, and the ability of the antibody to inhibit pathogen infection in a neutralization assay. For example, inbred mouse strains of varying H-2 haplotypes may be used for immunogenicity testing (several different strains are used because the T cell stimulating peptide may be presented with some, but not all MHC class II haplotypes). In particular, the vaccine may be administered subcutaneously in complete Freund's adjuvant or equivalent adjuvant, and groups of four animals are given either 4, 20, or 100 μg of the peptide vaccine. Two to three weeks later, the animals are challenged with a one-half dose of peptide emulsified in incomplete Freund's adjuvant. Seven to ten days later sera is collected.

IgG titers to the peptide vaccine may be determined in a standard ELISA assay. Briefly, ELISA plates (commercially available) are coated with the peptide vaccine at 1 μg/ml in phosphate-buffered saline (PBS). The coating solution is removed and unbound sites are blocked by the addition of 2% (w/v) powdered skim milk and the plates are subsequently washed three times with PBS containing 0.02% Tween 20 to remove any free peptide. Serial dilutions of sera are made and added to the peptide-coated wells. Following binding of the sera dilutions, unbound antibodies are washed out. Incubation with an enzyme-coupled anti-mouse IgG antibody is performed and is followed again by washing out unbound antibody. The amount of bound second stage antibody is determined by spectrophotometric readings following the addition of a chromogenic substrate. Results are calculated as reciprocal titers that give a reading above the background controls.

IgG titers to the native protein are similarly determined, except that the native protein is used to initially coat the titer wells. Because some fraction of native protein denatures upon contact with plastic, an alternative competitive binding assay can be performed. This is also a standardly performed assay and is identical to the direct ELISA except that, prior to addition of the anti-peptide antibodies, soluble antigens at concentrations ranging from approximately 100 uM to as little as 10 pM are added.

The virus neutralization assay of Wyatt et al. (*J. Virol.* 66:6997, 1992) provides a rapid complementation assay to measure inhibition of virus infection. Briefly, a chloramphenicol actyltransferase-expressing virus is incubated with antibody before exposure of the virus to target Jurkat lymphocytes. CAT activity in the target cells is measured in a standard way. The amount needed to inhibit virus entry by 50% is calculated. Alternatively, the sera samples can be incubated with HIV virus stocks prior to infection of HUT 78 cells. Infected cells are cultured for 7 days, and cell supernatants are assayed for virus antigens (p24E) using an ELISA assay (see Maeda et al., *AIDS Res. and Human Retroviruses* 8:2049–2054, 1992).

The following examples are offered by way of illustration, not limitation.

EXAMPLES

Example 1

Synthesis of Component Pieces

This example presents the synthesis of the component pieces which combine to form the conformationally constrained reverse-turn mimetics of the present invention.

A. Synthesis of First Component Pieces

The first component piece of this invention has the following structure 1:

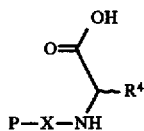

where R⁴ is an amino acid side chain moiety or derivative thereof, X is a chemical moiety selected from the moieties identified in Table 1, and P is an amino protective group suitable for use in peptide synthesis. The "X" moiety establishes the bridge between the first and third component pieces which defines the ring size of the conformationally constrained reverse-turn mimetic. The X moiety may be variable in length and flexibility, and thus effects the three-dimensional structure of the conformationally constrained reverse-turn mimetic.

The first component piece may be an N-protected hydrazine where the moiety X is a single nitrogen atom. Upon cyclization to the reverse turn mimetic, such a first component piece forms a hydrazide link with the carbonyl group of the third component piece. Alternatively, the first component piece may be an N-protected amine which upon cyclization forms an amide link. The synthesis of both general types of first compound pieces is set forth below.

(1) Synthesis of N-Protected Hydrazines (X=NH)

N-protected hydrazines for use as the first component piece may be made from their corresponding amino acids according to the procedures of Hoffman and Kim (*Tet. Lett.* 31:2953, 1990) and Vidal et al. (*J. Org. Chem,* 58:4791–4793, 1993). Briefly, an amino acid may be convened to the corresponding α-hydroxy methyl ester by reaction with sodium nitrite in aqueous sulfuric acid followed by treatment with diazomethane. The α-hydroxy group is displaced with mono-t-butyloxycarbonyl hydrazine after its conversion to trifluoromethanesulfonate with trifluoromethanesulfonic anhydride (with overall inversion of the amino acid configuration about the chiral carbon atom). The result is a first component N-protected hydrazine, a first component piece represented by formula 1 where the carboxylic acid group is protected as a methyl ester, X is NH, and P is the amino protective group, t-butyloxycarbonyl (BOC). The conversion of an amino acid to a representative first component N-protected hydrazine is shown below.

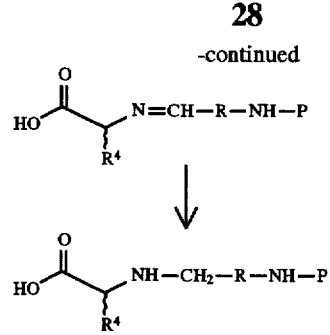

(2) Synthesis of First Component N-Protected Amines (X=NHRCH₂)

Reductive amination. A variety of first component pieces may be prepared from suitable aldehydes by a facile reductive amination process, as described by Gribble and Nutatitis (*Org. Prep. Proced. Int.* 17:317, 1985) or Sasaki and Coy (*Peptides* 8:119, 1987). In this method, reaction of the amino group of an amino acid with the carbonyl group of an aldehyde results in the formation of an imine which may be subsequently reduced with an appropriate hydride reducing agent to provide a C—N link. To produce such a first component piece of the present invention, the requisite aldehyde bears a N-protected amino group. The synthesis of first component N-protected amines by general method of reductive amination is presented schematically below (with overall retention of the amino acid configuration about the chiral carbon atom):

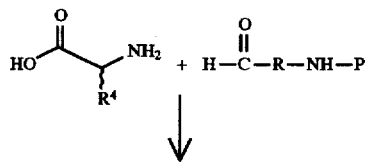

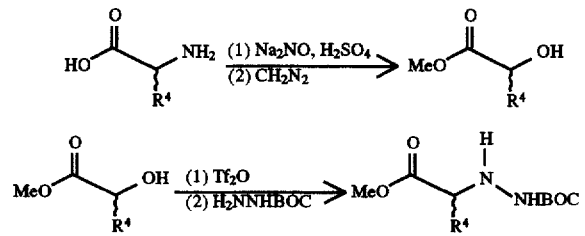

The N-protected amino aldehyde shown above may be represented with the general formula, P—NH—R—CHO, where P is an amino protecting group and R is a chemical moiety (for example, —CH₂—, —C(CH₃)₂—, —CH=CHC(CH₃)₂—, or —CH₂CH₂C(CH₃)₂—) which links the aldehyde carbonyl with the N-protected amino group. The product of the reductive amination shown above yields the first component piece of structure 1 when X is NH—R—CH₂.

Synthesis of aldehydes from amino acids. The preparation of first component pieces with variable X by the reductive amination method requires the synthesis of suitable aldehydes, i.e., aldehydes which bear N-protected amino groups. Such suitable aldehydes may be directly prepared from their corresponding amino acids by a two step procedure as described by Goel et al. (*Org. Syn.* 67:69, 1988). In a typical reaction sequence, an N-protected amino acid is first converted to a mixed anhydride by treatment with methyl chloroformate and treatment with N,O-dimethylhydroxylamine provides the corresponding carboxamide, which is followed by reduction to the aldehyde with lithium aluminum hydride. The conversion of an N-protected amino acid to its corresponding N-protected aldehyde, as described above, is illustrated schematically by the following reaction:

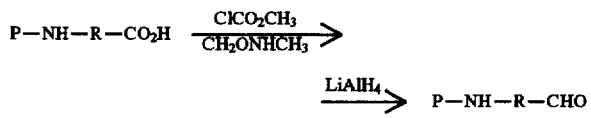

where P and R are as described above. The synthesis of suitable N-amino protected aldehydes is presented as sections (a)–(d) below.

(a) First Component N-Protected Amines (X=NHCH₂CH₂)

In this example, the aldehyde is an N-protected 2-aminoethanol and may be prepared from its corresponding N-protected amino acid, glycine, according to the process of Goel et al. as described in section (2) above. N-BOC-glycine is commercially available from a variety of sources and is suitable for conversion to its aldehyde, BOC—NH—CH₂—CHO. Treatment of the resulting aldehyde, N-BOC-aminoacetaldehyde, with an amino acid under the reductive amination conditions as described in (2) above yields the first component N-protected amine shown below, which is the first component piece of general formula 1 when X is —NHCH₂CH₂— and P is the BOC protecting group:

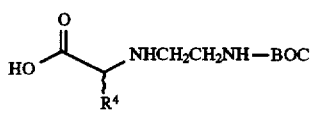

(b) First Component N-Protected Amines (X=NHC(CH₃)₂ CH₂)

In this example, the aldehyde is an N-protected 2-amino-2-methylpropanol, and may be prepared from its corresponding N-protected amino acid, 2-methylalanine, according to the process of Goel et al. as described in section (2) above. N-BOC-2-methylalanine is commercially available from a variety of sources and is suitable for conversion to its aldehyde, BOC—NH—C(CH₃)₂—CHO. Treatment of the resulting aldehyde, N-BOC-2-amino-2-methylpropanal, with an amino acid under the reductive amination conditions as described in section (2) above yields the first component N-protected amine shown below which satisfies the first component piece of general formula 1 where X is NHC(CH₃)₂CH₂.

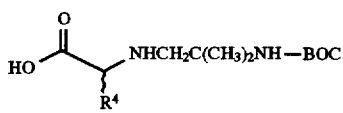

(c) First Component N-Protected Amines (X=NHC(CH₃)₂ CH=CHCH₂)

Extension of the length and adjustment of the flexibility of linker X may be achieved by homologation of the aldehydes described above. For example, the homologation of the aldehyde intermediate in section (2)(b) above by Wittig reaction provides a vinylogous analog as described in House and Rasmusson (J. Org. Chem. 26:4278, 1961).

Briefly, treatment of N-BOC-2-amino-2-methylpropanal, from section (2)(b) above, with methyl (triphenylphosphoranylidene) acetate results in the extension of the carbon chain of the aldehyde by two carbons. The reaction is represented schematically as folows.

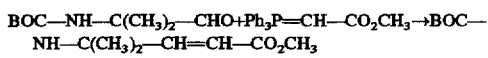

The ester product above may then be hydrolyzed under basic conditions to yield the corresponding N-BOC amino carboxylic acid, which may then be directly converted to the aldehyde by the reductive method of Goel et al. as described above in section (2). Conversion of the carboxylic acid derived from the above ester to the corresponding aldehyde is illustrated below.

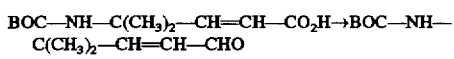

Treatment of the vinylogous aldehyde with an amino acid under the reductive amination conditions as described in section (2) above yields the first component N-protected amine shown below, which satisfies the first component piece general formula 1 when X is NHC(CH₃)₂ CH=CHCH₂:

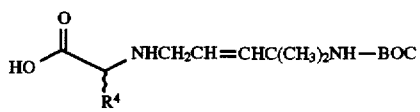

(d) First Component N-Protected Amines (X=NHC(CH₃)₂ CH₂CH₂CH₂)

The X moiety of section (2)(c) above contains a vinyl group which imparts some rigidity to the linker moiety. A more flexible linker may be prepared by hydrogenation of the N-protected vinylogous aldehyde described above. Hydrogenation to the vinylogous aldehyde produces the saturated analog shown below.

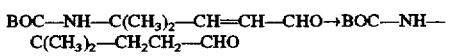

Treatment of the saturated aldehyde with an amino acid under the reductive amination conditions as described in section (2) above yields the first component N-protected amine shown below, which satisfies the first component piece general formula 1 when X is NHC(CH₃)₂ CH₂CH₂CH₂:

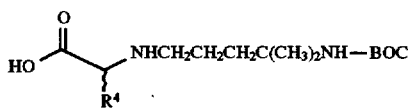

B. Synthesis of Second Component Pieces

The second component pieces of this invention may have any one of the following structures 2a, 2b or 2c:

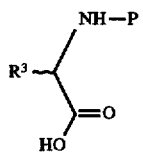  2a

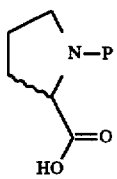  2b

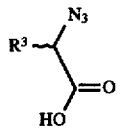  2c where $R^3$ is an amino acid side chain moiety or derivative thereof, and P is an amino protective group suitable for use in peptide synthesis. Structure 2a is a generalized representation of an N-protected amino acid and structure 2b represents an N-protected proline derivative. Suitable second component pieces, 2a and 2b, are commercially available. For example, FMOC amino acids are available from a variety of sources. Alternatively, these or other N-protected amino acids may be readily prepared by standard organic synthetic techniques.

Second component piece 2c is an azido derivative of an amino acid. In this amino acid derivative, the α-amino group has been substituted with an azido group. The azido derivative of an amino acid may be prepared by the following reaction (Zaloom et al., J. Org. Chem. 46:5173–5176, 1981):

C. Synthesis of Third Component Pieces

The third component piece may have any one of the following structures:

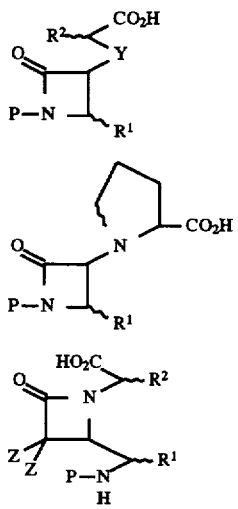

where $R^1$ and $R^2$ are an amino acid side chain moieties or derivatives thereof, Y is —$CH_2$—, —NZ—, —O— or —S—, Z is H or —$CH_3$, and P is an amino protective group suitable for use in peptide synthesis. Preferred protective groups include t-butyl dimethylsilyl (TBDMS), BOC and FMOC.

More specifically, third component piece 3(a) may have any one of the following structures:

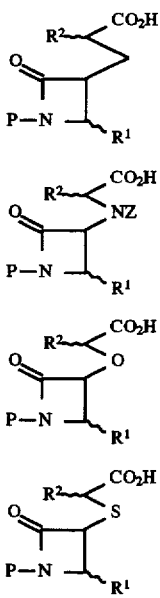

The third component pieces of the present invention are β-propiolactam derivatives, also commonly known as 2-azetidinone derivatives. Third component pieces 3a are analogous azetidinones which differ in the nature of the atom connecting the azetidinone ring with the carboxylic acid portion of the molecule. The atom connecting the two portions of these third component pieces are C, N, O and S for 3(a1), 3(a2), 3(a3) and 3(a4), respectively. Third component piece 3b is a derivative of 3a(2), wherein $R^2$ is proline. Third component piece 3c is a 2-substituted azetidinone in which the azetidinone nitrogen is also the α-amino group of an α-amino acid. Representative syntheses of these third component pieces 3a–3c follows.

(1) Synthesis of Third Component Piece 3(a1)

Third component piece 3(a1) may be prepared by the method as generally described in Williams et al., *J. Amer. Chem. Soc.* 111:1073, 1989. The synthesis of 3(a1) is presented schematically below.

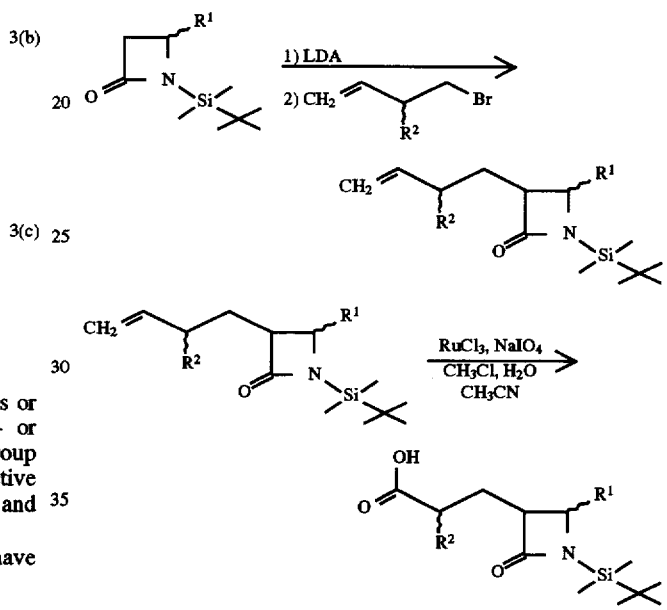

Briefly, the anion of an N-TBDMS-2-azetidinone generated by treatment with lithium diisopropylamide is alkylated with a 4-bromobutenyl derivative to yield the corresponding 4-butenyl azetidinone. Oxidative cleavage of the terminal alkene with ruthenium tetroxide provides third component piece 3(a1), where P is the TBDMS protective group.

(2) Synthesis of Third Component Piece 3(a2)

Third component piece 3(a2) may be prepared by the method as generally described in Miller et al. (*J. Amer. Chem. Soc.* 102:7026, 1980). The synthesis of 3(a2) is presented schematically below.

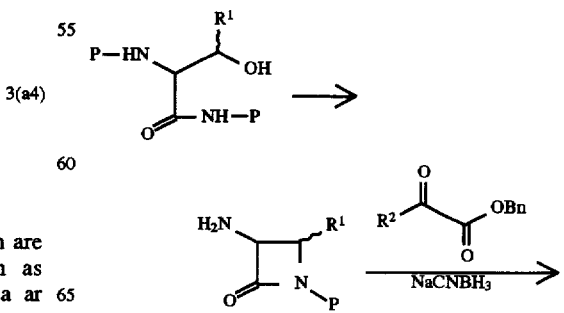

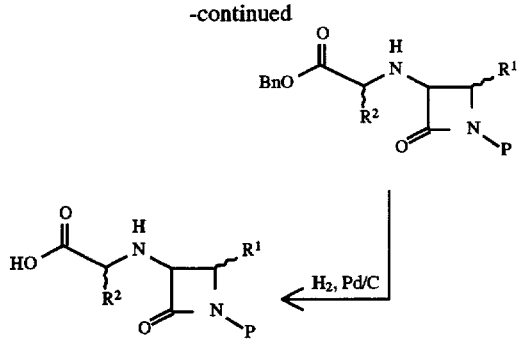

Briefly, the cyclization of a β-hydroxy amide derivative provides an 4-amino-2-azetidinone. Condensation of the azetidinone amino group with an α-keto benzyl ester derivative, and concommitant reduction with sodium cyanoborohydride, yields an ester of 3(a2). Hydrogenolysis of the benzyl protecting group produces third component piece 3(a2).

(3) Synthesis of Third Component Piece 3(a3)

Third component piece 3(a3) may be prepared by the method as represented schematically below:

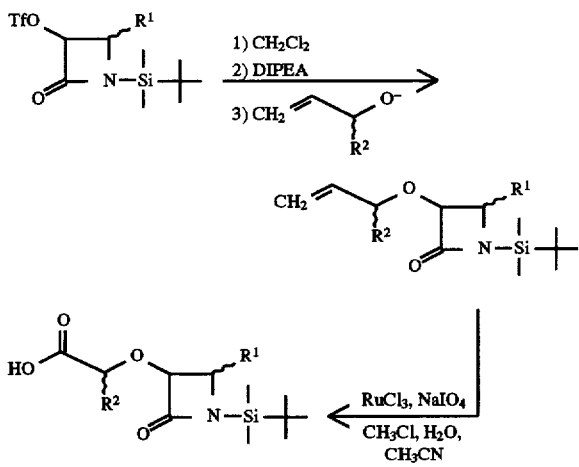

Briefly, displacement of the trifluoromethane sulfonate group from a 4-trifluoromethanesulfonyl-2-TBDMS-2-azetidinone derivative (from hydroxy azetidinone) by the oxyanion of an allyl alcohol provides a terminal alkene of 3(a3). Oxidative cleavage of the terminal alkene with ruthenium tetroxide provides carboxylic acid 3(a3).

(4) Synthesis of Third Component Piece 3(a4)

Third modular component piece 3(a4) is made in the same manner as 3(a3), except POC(O)CH(R²)S⁻ is added in place of the allyl alcohol, and the resulting ester is hydrolysed to yield 3(a4).

(5) Synthesis of Third Component Piece 3b

Third modular component piece 3b is made in the same manner as 3(a3), except an ester of proline is added in place of the allyl alcohol, and the resulting ester is hydrolysed to yield 3(b).

(6) Synthesis of Third Component Piece 3c

Third component piece 3c may be prepared by the method as generally described in Hart and Hu (*Chem. Rev.* 89:1447, 1990). The synthesis of 3c is presented schematically below:

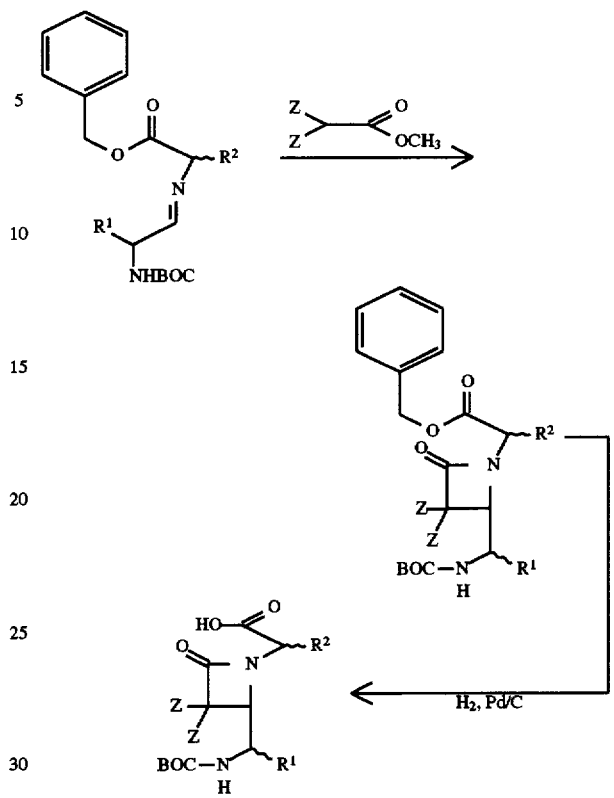

Briefly, the imine product of the condensation of the α-amino group of a amino acid benzyl ester with the carbonyl group of an N-BOC protected aldehyde derived from an α-amino acid was treated with the enolate of methyl isobutyrate to yield a 4,4-dimethyl-2-azetidinone derivative. Hydrogenolysis of the benzyl protecting group provides third component piece 3c where P is a BOC protecting group and Z is methyl.

Alternatively, treatment of the imine above with the enolate of methyl acetate followed by hydrogenolysis provides third component piece 3c where Z is hydrogen.

Example 2

The Coupling of First, Second and/or Third Component Pieces

The coupling of the component pieces to produce the reverse-turn mimetics of the present invention generally involve the formation of amide bonds. The amide bonds which link the pieces may be formed by standard synthetic peptide techniques and may be performed by either liquid or solid phase synthesis.

Typically, in the solid phase synthesis of a peptide containing a conformationally constrained reverse-turn mimetic, the first component piece is incorporated into the peptide sequence at a specific point in the synthesis. Once the first component piece is incorporated, the synthesis of the remainder of the mimetic turn follows. For example, for a conformationally constrained beta-turn mimetic, the turn is synthesized by subsequent coupling of a second and a third component piece, followed by cyclization of the first component piece to the third component piece. The remainder of the peptide may then be synthesized by further elongation of the peptide chain via continued step-wise coupling of the remaining amino acids.

A. Representative Coupling of First and Second Component Pieces

The coupling of the first and second component pieces provides a combined first-second intermediate. Three different combined first-second intermediate species may be formed by coupling the first component piece 1 with second component pieces 2a, 2b or 2c. The coupling products, identified as 1-2a, 1-2b, and 1-2c, are shown below.

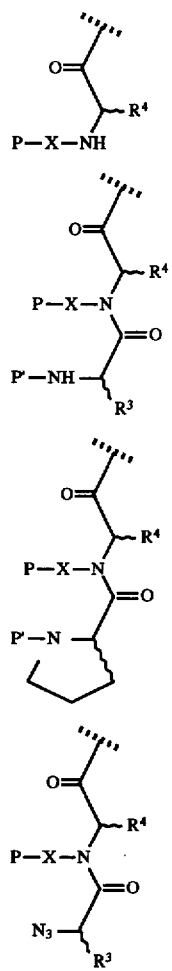

In the above representation, P is BOC and P' is FMOC.

The coupling of of the first and second component pieces may be accomplished by a silicon mediated acid fluoride coupling. In this coupling procedure, solid phase immobilized 1 is converted to the corresponding N-trimethylsilyl derivative (1a below) by treatment with 5 equivalents of bis(trimethylsilyl)acetamide.

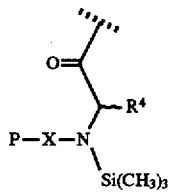

Reaction of either of the acid fluorides of 2a–2c with N-silyl derivative 1a yields combined first-second intermediate 1-2a, 1-2b, or 1-2c, respectively. The acid fluorides of 2a–2c may be readily prepared from the corresponding carboxylic acids by cyanuric fluoride treatment according to general method as described by Carpino and Han (*J. Amer. Chem. Soc.* 112:9651-52, 1990).

(1) Peptide Coupling with N-FMOC Protected Amino Acids

The general silicon mediated acid fluoride peptide coupling procedure described above may be utilized to couple N-protected amino acid fluorides (such as 2a or 2b) with N-silyl peptides (such as 1a). For peptide synthesis in the liquid phase, N-protected amino acid fluorides are coupled to carboxy protected N-silyl amino acids. The silicon mediated acid fluoride coupling method represents an advancement over traditional amide forming reactions which employ coupling agents such as carbodiimides or mixed anhydride reagents. These reagents activate the carboxyl group of an amino acid for coupling with the amino group of another amino acid.

Despite the improvements and advantages that the silicon mediated acid fluoride coupling offers, in some instances, peptide bond formation remains difficult due to the steric interaction between the amino acid side chain of the N-silyl peptide and the traditional bulky N-FMOC (fluorenylmethoxycarbonyl) protecting group of the incoming carboxy activated amino acid. In fact, reaction rates for the coupling of amino acids with relatively bulky side chains (such as histidine, phenylalanine, trytophan, tyrosine, arginine, leucine, isoleucine, glutamine, asparagine, aspartic acid, glutamic acid and threonine) are significantly less compared with those amino acids having relatively less sterically demanding side chains such as glycine, alanine, and serine in coupling reactions which utilize N-FMOC protected amino acids.

Peptide bond formation with secondary amines such as 1a is also more difficult for steric reasons. The additional amino substitutent significantly increases the steric hinderance of the amine group and diminishes its nucleophilicity (ability to form peptide bond with a carboxy derivative). The diminution of reactivity is manifested in slow reaction rates. This difficulty in peptide coupling is especially true in reactions with N-FMOC protected amino acids.

(2) Peptide Coupling with Azido Acid Fluorides

The steric problems associated with peptide coupling of bulky N-FMOC protected amino acid fluorides can be eliminated by the use of the corresponding azido acid fluorides. In contrast to the FMOC group, the azido group is a small (3 nitrogen atoms), linear substituent. The α-amino group of an amino acid in the former acid fluorides are simply protected by a group (FMOC) which prevents interference in the peptide coupling reaction. Once coupled, the protecting group is removed and subsequent couplings performed. In contrast, in azido acid fluorides, the α-amino group of an amino acid has been transformed to an azido group ($N_3$). After coupling with the azido acid fluoride, the azido group may be directly activated for subsequent couplings. The overall result for either acid fluoride reagent is peptide bond formation. However, the azido acid fluoride reagent does not suffer from the problems of steric inhibition of peptide bond formation associated with N-FMOC protected amino acids.

Accordingly, azido acid fluorides are the reagents of choice for sterically demanding peptide bond formation. These couplings include reactions of amino acids with sterically bulky side chain moieties and amide bond formation with secondary amines. The structures of these acid fluorides is shown below (R represents an amino acid side chain moeity or derivative thereof).

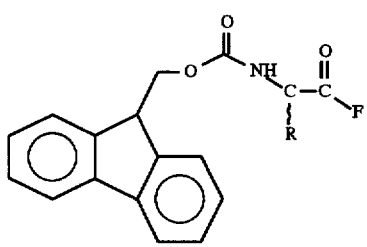

N—FMOC Protected Acid Fluoride

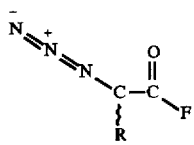

Azido Acid Flouride

The azido acid fluorides may be prepared from their corresponding azido acids, and the azido acids may be readily synthesized from the corresponding amino acids, by standard methods as disclosed above.

As mentioned above, unlike N-protected amino acid derivatives which must be deprotected prior to subsequent coupling, azido acids may be directly activated for peptide coupling with a subsequent amino acid. Treatment of the azido peptide with triphenyl phosphine generates a phosphine imine which, upon reaction with an amino acid or a second or third component piece of the present invention yields a peptide bond and the corresponding chain lengthened peptide. The process is generally illustrated below where R. is an amino acid side chain moeity:

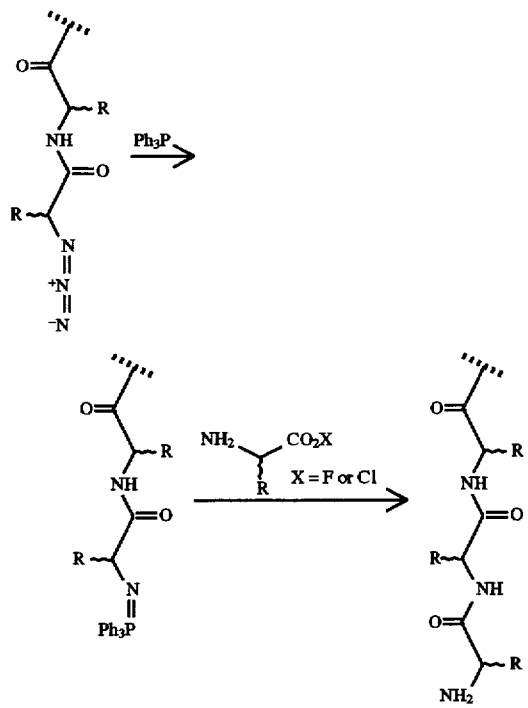

The azido add fluoride peptide coupling method described above has utility in peptide coupling in general and, more specifically, in the practice of the present invention. This method is further illustrated for coupling of the modular component pieces of the present invention in sections C, D, and E below.

B. Representative Coupling of First and Third Component Pieces

The coupling of the first modular component and third modular component pieces provides a combined first-third intermediate. Six different combined first-third intermediate species may be formed as result of the coupling of first component piece 1 with either third component piece 3(a1), 3(a2), 3(a3), 3(a4), 3b, or 3c. The coupling products, identified as 1-3(a1), 1-3(a2), 1-3(a3), 1-3(a4), 1-3(b), and 1-3(c), are shown below:

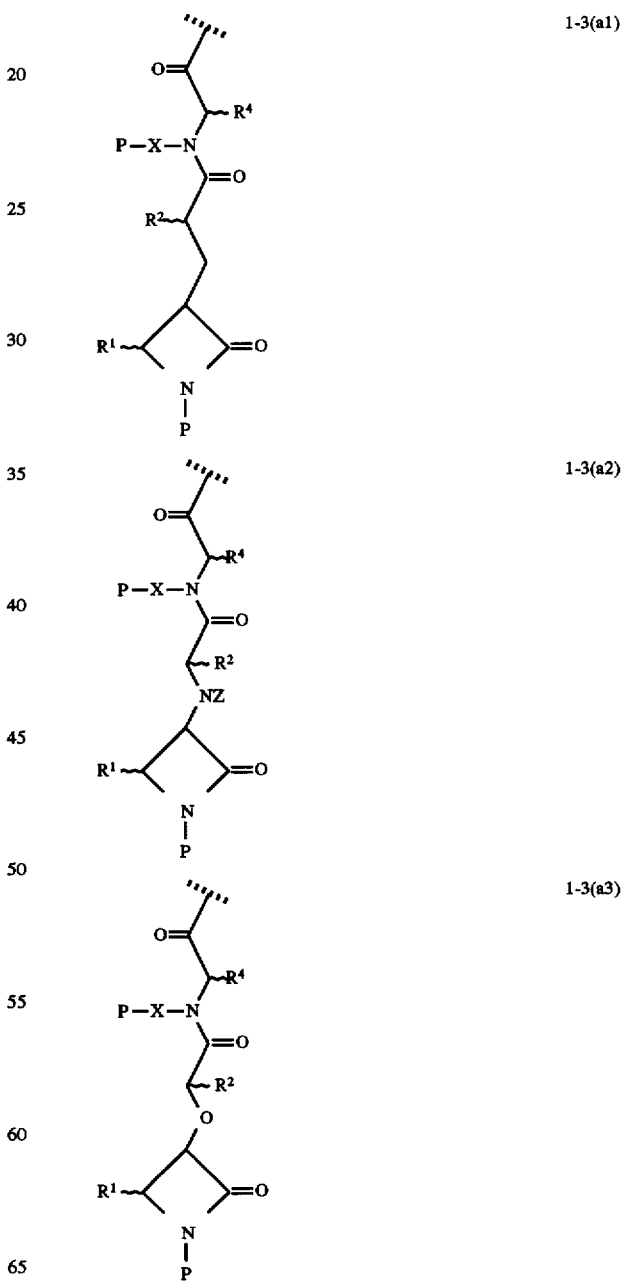

1-2(a)-3(a2), 1-2(a)-3(a3), 1-2(a)-3(a4), 1-2(a)-3(b), and 1-2(a)-3(c), are shown below:

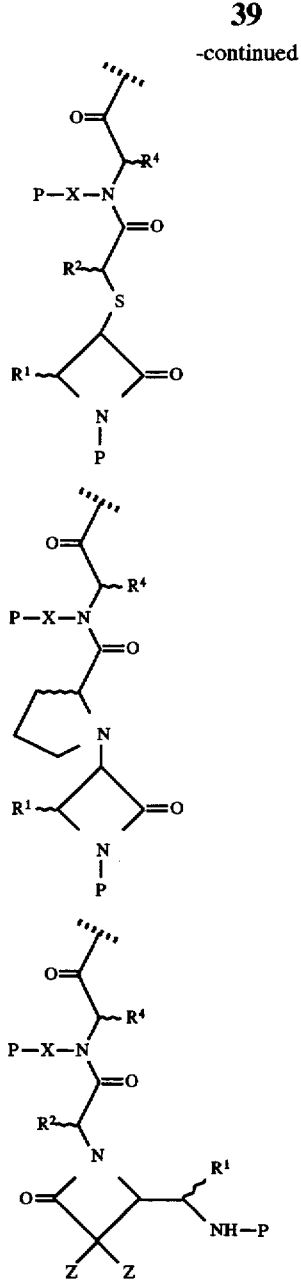

In the above representation, P is a protective group suitable for use in peptide synthesis, X is a linker as described in Example 1, and $R^1$, $R^2$, $R^3$ and $R^4$ represent an amino acid side chain moiety.

The coupling of the first and third component pieces is accomplished by the silicon mediated acid fluoride method as described in section A above via N-silyl derivative 1a. The combined first-third intermediates are precursors for conformationally constrained gamma-turn mimetic synthesis.

C. Representative Coupling of a Combined First-Second Component Intermediate with a Third Component Piece The coupling of a combined first-second intermediate with a third modular component piece provides a combined first-second-third intermediate. Eighteen different combined first-second-third intermediate species may be formed as result of coupling each of the three first-second intermediates 1-2(a), 1-2(b), or 1-2(c) with each of the six third component pieces 3(a)-3(c). The products of coupling 1-2(a) with 3(a)-3(c), a representative set of first-second-third intermediate coupling products, identified as 1-2(a)-3(a1), In the above structures, P is a protective group suitable for use in peptide synthesis, X is a linker as described in Example 1, Z is either hydrogen or methyl, and R represents an amino acid side chain moiety. The remaining ten firstsecond-third intermediates, formed from coupling of 1-2(b) and 1-2(c) with 3(a)-3(c), would have structures analogous to those represented above.

For couplings involving 1-2(b) derivatives, the coupling of a combined first-second intermediate with a third component piece may be accomplished by traditional peptide coupling techniques such as those performed on automated peptide synthesizers. Briefly, the steps include N-deprotection of the combined first-second intermediate, addition and carboxyl group activation of the third component piece which results in peptide bond formation and coupling.

Alternatively, for couplings which involve 1-2(c) derivatives, the couplings are readily achieved via triphenyl phosphine activation as described above in section A(2).

The combined first-second-third intermediates are precursors required for conformationally constrained beta-turn mimetic synthesis.

D. Representative Coupling of a Combined First-Second Component Intermediate with a Second Component Piece The coupling of a combined first-second intermediate with a second modular component piece provides a combined first-second-second intermediate. Nine different combined first-second-second intermediate species may be formed as result of the coupling each of the three first-second intermediates 1-2(a), 1-2(b), or 1-2(c) with each of the three second component pieces 2(a)-2(c). The products of coupling with 2(a)-2(c), a representative set of first-second-second intermediate coupling products, identified as 1-2(a)-2(a), 1-2(a)-2(b), and 1-2(a)-2(c), are shown below.

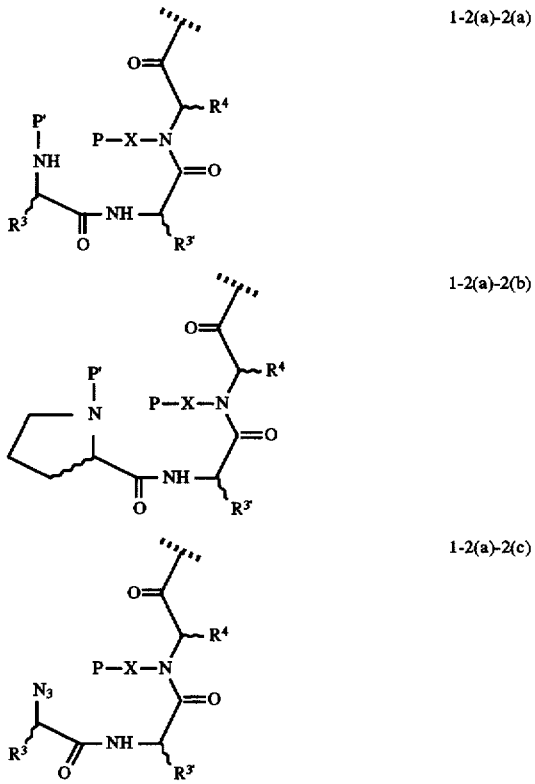

In the above representation, P is a protective group suitable for use in peptide synthesis, X is a linker as described in Example 1, and R represents an amino acid side chain moiety. The remaining first-second-second-third intermediates, formed from coupling of 1-2(b) and 1-2(c) with 2(a)-2(c), would have structures analogous to those represented above.

The coupling of a combined first-second intermediate with a second component piece may be accomplished by the peptide coupling techniques described in C above.

E. Representative Coupling of a Combined First-Second-Second Component Intermediate with a Third Component Piece The coupling of a combined first-second-second intermediate with a third modular component piece provides a combined first-second-second-third intermediate. Forty-five different combined first-second-second-third intermediate species may be formed as result of the coupling each of the nine first-second-second intermediates 1-2(a)-2(a), 1-2(a)-2(b), 1-2(a)-2(c), 1-2(b)-2(a), 1-2(b)-2(b), 1-2(b)-2(c), 1-2(c)-2(a), 1-2(c)-2(b), and 1-2(c)-2(c) with each of the five third component pieces 3(a)-3(c). The products of coupling 1-2(a)-2(a) with 3(a1), a representative species of first-second-second-third intermediate coupling products, identified as 1-2(a)-2(a)-3(a1), is shown below:

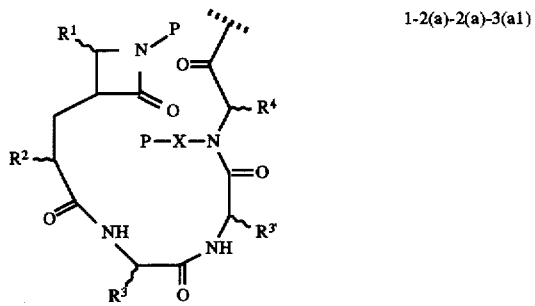

In the above representation, P is a protective group suitable for use in peptide synthesis, X is a linker as described in Example 1, and R represents an amino acid side chain moiety. The remaining first-second-second-third intermediates, would have structures analogous to those represented above.

The coupling of a combined first-second-second intermediate with a third component piece may be accomplished by the peptide coupling techniques described in C above.

The combined first-second-second-third intermediates are precursors required for conformationally constrained beta-bulge mimetic synthesis.

Example 3

Cyclization of Combined Component Pieces to Form Conformationally Constrained Reverse-Turn Mimetics The cyclization of the first and third modular component pieces through covalent coupling of linking group X of the first component piece with the carbonyl carbon of the azetidinone group of the third component piece yields the conformationally constrained reverse-turn mimetics of the present invention. The presence of component pieces between the first and third component pieces determines the nature of the conformationally constrained reverse-turn mimetic (i.e., beta-turn, gamma-turn or beta-bulge mimetic).

Cyclization of the first component piece to the third component piece involves removal of protecting group P from linking group X of the first component piece. As described in Example 1A, P is an amino protective group, typically a BOC group. Therefore, treatment of the combined intermediate with TFA in $CH_2Cl_2$ and subsequent neutralization with DIPEA removes the protecting group and provides linking group X, which bears a nucleophilic nitrogen. Depending upon the nature of X, the nucleophilic nitrogen is either a hydrazine, Example 1A(1), or an amine, Example 1A(2)(a–d).

The nucleophilic hydrazine or amine of the first component piece results in facile cyclization to the hydrazide or amide, respectively. The ease of cyclization is due to the proximity and the electrophilic nature of the azetidinone carbonyl of the third component piece.

A. Representative Conformationally Constrained Beta-Turn: Cyclization of a Combined First-Second-Third Modular Component N-deprotection and cyclization of the first-second-third combined intermediate provides the beta-turn mimetic. The combined intermediate may be any one of those described above in Example 2C. For example, aqueous acid treatment of 1-2(a)-3(a1), for a species where X=—NH—, results in cyclization to the conformationally constrained beta-turn mimetic shown below:

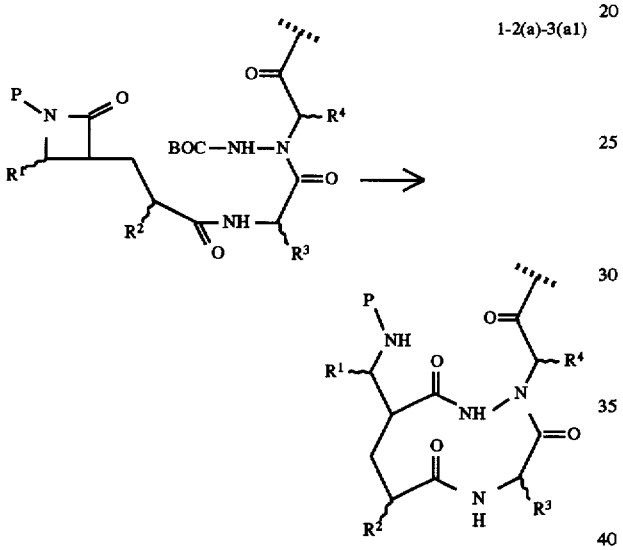

The cyclization depicted above is representative for all beta-turn mimetic cyclizations of the present invention.

B. Representative Conformationally Constrained Gamma-TurnMimetic: Cyclization of a Combined First-Third Modular Component N-deprotection and cyclization of a first-third combined intermediate provides the gamma-turn mimetic. The combined intermediate may be any one of those described above in Example 2B. For example, aqueous acid treatment of 1-3(a1), for a species where X=—NH—, results in cyclization to the conformationally constrained gamma-turn mimetic shown below:

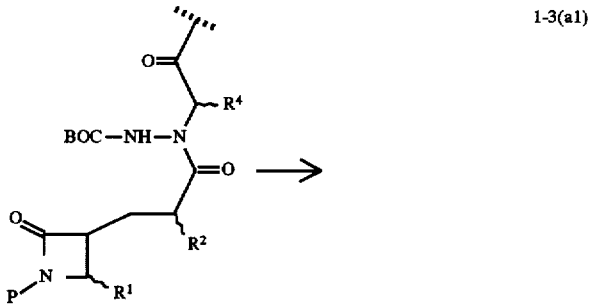

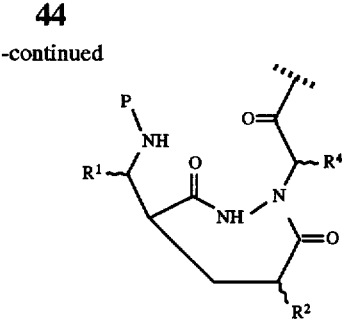

The cyclization depicted above is representative for all gamma-turn mimetic cyclizations of the present invention.

C. Representative Conformationally Constrained Beta-Bulge Mimetic: Cyclization of a Combined First-Second-Second-Third Modular Component N-deprotection and cyclization of a first-second-second-third combined intermediate provides the beta-bulge mimetic. The combined intermediate may be any one of those described above in Example 2E. For example, TFA/$CH_2Cl_2$ treatment and neutralization of 1-2(a)-2(a)-3(a1), for a species where X=—NH—, results in cyclization to the conformationally constrained beta-bulge mimetic shown below.

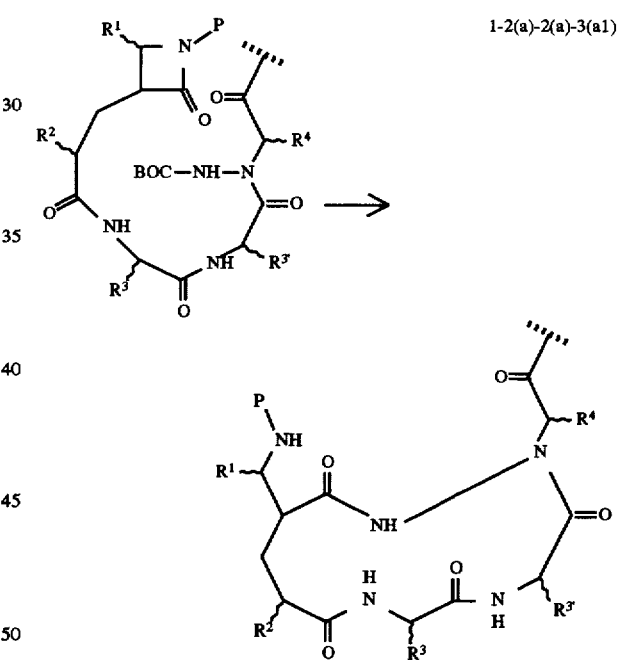

The cyclization depicted above is representative for all beta-bulge mimetic cyclizations of the present invention.

Example 4

Synthesis of a Conformationally Constrained Reverse-Turn Which Mimics an Antigenic Determinant of HIV Virus This example presents the synthesis of a conformationally constrained reverse-turn which mimics an antigenic determinant of HIV. In this example, the reverse-turn is a beta-turn mimetic to the V3 loop conformation of amino acids 306 to 317 of gp120 (i.e., RKRIHIGPGRAF) (SEQ ID NO.1) which contains the IGPG-turn (SEQ ID NO.16). The beta-turn mimetic is prepared by cyclization of a combined first-second-third modular component where the individual components are determined by the peptide sequence of the antigenic determinant of the virus. Accordingly, the specific combined first-second-third modular component contains a first component piece 1 wherein $R^4$ is hydrogen, X is —NH—, and P is BOC; a second component piece 2(b) wherein P is an FMOC or other suitable amine protecting group; and a third component piece 3(a1) where $R^2$ is hydrogen, $R^1$ is the isoleucine side chain (—CH(CH$_3$)CH$_2$CH$_3$), and P is an FMOC or a suitable amine protecting group.

The combined first-second-third modular component as described above may be prepared as generally described in Examples 1 through 3 above. Specifically, first component piece 1 ($R^4$=H, X=—NH—, P=BOC) may be prepared according to the synthesis described in Example 1A(1) utilizing glycine as the starting material. Hydrolysis of the resulting methyl ester to the corresponding acid yields first component piece 1 ($R^4$=H, X=—NH—, P=BOC) which is ready for peptide coupling. First component piece 1 may be directly coupled to an amino group of another peptide, such as one immobilized on a solid support by standard techniques (e.g., the N-terminal amine acid of a peptide immobilized on a solid-phase in traditional peptide synthesis). Second component piece 2(b); an N-protected proline derivative such as N-FMOC proline (commercially available) may then be coupled to first component piece 1 (now the N-terminus of the peptide immobilized on solid-phase) as described in Example 2A(1) to yield a solid-phase immobilized combined first-second modular component 1-2(b) ($R^4$=H, X=—NH—, P=BOC, P'=FMOC). Third component piece 3(c) ($R^2$=H, $R^1$=—CH(CH$_3$)CH$_2$CH$_3$, Z=H, and P=BOC) may be prepared according to the synthesis described in Example 1C(5), utilizing glycine, isoleucine, and methyl acetate as starting materials. This third component piece 3(c) may be directly coupled to the N-terminus of solid-phase immobilized combined first-second modular component 1-2(b) by standard peptide coupling techniques as described in Example 2(C) to yield a solid-phase immobolized combined first-second-third modular component 1-2(b)-3(c) ($R^4$=H, X=—NH—, P=BOC, $R^2$=H, $R^1$=—CH(CH$_3$)CH$_2$CH$_3$, Z=H, P'=FMOC). Treatment of solid-phase immobilized 1-2(b)-3(c) with aqueous acid (as described in Example 3A) effects cyclization to a conformationally constrained beta-turn mimetic ($R^4$=H, X=—NH—, $R^2$=H, $R^1$=—CH(CH$_3$)CH$_2$CH$_3$, Z=H, P=FMOC), IGPG-turn (SEQ ID NO.16), immobilized on a solid-phase. Alternatively, the above-described synthesis may be carried out in solution phase (i.e., without solid-phase immobilization as is employed in automated peptide synthesis) by the reactions described above and standard synthetic organic techniques.

At this stage, the beta-turn mimetic may be either cleaved from the solid phase or additional amino acids may be coupled to the beta-turn mimetic by standard solid-phase peptide synthetic techniques (see Example 5 below which describe the syntheses of peptide vaccines based on immobilized beta-turn mimetics).

Example 5

Synthesis of a Peptide Vaccine to HIV

The synthesis of a peptide vaccine to HIV is disclosed in this example. In particular, the reverse-turn mimetic of this example corresponds to the peptide sequence RKRIHIG-PGRAF (SEQ ID NO.1) having a conformationally constrained beta-turn substituted for the IGPG-turn (SEQ ID NO.16). The cleavable linker in this example is the sequence FYLKRKR (SEQ ID NO.14), and the T cell stimulating peptide is the sequence GPKEPFRDYVDRFY (SEQ ID NO.17). The HIV vaccine of the present invention may be synthesized by automated solid-phase peptide synthetic methods using standard peptide reagents and component pieces of this invention.

The synthesis of the vaccine begins with the selection of a phenylalanine immobilized solid-phase to which amine acids will be subsequently and sequentially coupled. The first amino acid to be coupled to the solid phase is alanine which is followed by arginine. At this stage in the synthesis, the solid-phase bears an immobilized tripeptide (FAR) with an arginine N-terminus. Referring to the vaccine sequence identified above, incorporation of the beta-turn mimetic follows. The beta-turn (i.e., GPGI) (SEQ ID NO.18) is accomplished in a stepwise manner as described above in Example 4 to yield a heptapeptide (FARGPGI) (SEQ ID NO.19) immobilized on the solid-phase. The extension of the peptide chain of the vaccine continues by coupling the remaining amino acids to yield the peptide sequence of the virus' antigenic determinant (i.e., by the sequential addition of the amino acids H,I,R,K,R) to provide the immobilized dodecapeptide (FARGPGIHIRKR) 9SEQ ID NO.20). The addition of amino acids to provide a suitable cleavable linker follows (i.e., the addition of amino acids K and L) to yield immobilized FARGPGIHIRKRKL (SEQ ID NO.21). The sequential addition of the remaining amino acids of the vaccine corresponding to the T cell stimulatory peptide to the immobilized peptide completes the coupling stage of the synthesis. Release of the peptide from the solid phase yields the vaccine. Alternatively, and in a preferred embodiment, rather than performing the entire synthesis on a solid phase support, the conformationally constrained reverse-turn mimetic is made in solution. The peptide sequences attached to the C- and N-terminus thereof are synthesized on the solid support, removed from the solid support, and coupled in solution to the conformationally constrained reverse-turn mimetic by known coupling techniques.

Example 6

Activity of Peptide Vaccine to HIV

The immunogenicity of the peptide vaccines of this invention may generally be determined for HIV as follows. Antisera is raised in mice and guinea pigs by immunization with the peptide vaccine of Example 5 in various adjuvants including, for example, alum, CFA (complete Freund's adjuvant) and Quil A, at a dosage of 25, 50 or 100 μg per injection. Animals are periodically bled and reboosted during a period of one year in order to follow immunologic memory. The ability of antisera raised against the peptide vaccine to elicit anti-V3$_{MN}$ specific antibodies, as well as antibodies cross-reactive with the V3 regions of other HIV-1 isolates, are determined by ELISA techniques using a panel of eight linear V3 peptides as the target antigens. When permitted, ELISA measurements are also performed with recombinant gp120 and/or gp160 as the target antigen. Functional activities of antisera raised against the peptide vaccine are determined by in vitro virus neutralization and syncytia inhibition assays using a series of HIV-1 isolates.

Example 7

Synthesis of a Peptide Vaccine to Influenza

In this example, the synthesis of a peptide vaccine to influenza is disclosed. The peptide vaccine contains a conformationally constrained reverse-turn which mimics an antigenic determinant of the influenza virus. Specifically, the reverse-turn is a beta-turn mimetic to the hemagluttinin (HA) loop conformation of amino acids 140 to 146 (i.e., KRGPGSG) (SEQ ID NO.3) which contains the RGPG-turn (SEQ ID NO.22). As mentioned above, the hemagglutinin surface protein of influenza virus has been shown by X-ray crystallography to contain the RGPG-tun (SEQ ID NO.22) (Wilson et al., *Nature* 289:368-373, 1981). Therefore, a beta-turn mimetic of this invention is prepared by cyclization of a combined first-second-third modular component where the individual components are determined by the peptide sequence of the antigenic determinant of the influenza virus.

For example, the beta-turn mimetic for the RGPG-turn, (SEQ ID NO.22) may be synthesized in the same manner as described above in Example 4. The only difference in the two syntheses is that the third component piece required for the beta-turn RGPG (SEQ ID NO.22) mimetic is 3(a1) wherein $R^2$ is hydrogen, $R^1$ is the arginine side chain (—(CH$_2$)$_3$NHC(NH)NH$_2$), and P is an FMOC or other suitable amine protecting group. The third component piece 3(a1) may be prepared as described in Example 1C(1). Accordingly, the beta-turn mimetic for the RGPG-turn (SEQ ID NO.22) may be prepared as described in Example 4 utilizing third component piece 3a ($R^1$=—(CH$_2$)$_3$NHC(NH)NH$_2$, $R^2$=H, P=FMOC).

In addition to the RGPG-turn, (SEQ ID NO.22) NMR studies have also indicated the presence of a "back-shifted" GPGS-turn (SEQ ID NO.23) (Kieffer et al., *J. Biomolecular NMR* 3:91-112, 1993). Accordingly, beta-turn mimetics are synthesized for the GPGS-turn (SEQ ID NO.23) in the same manner as described above for the RGPG-turn (SEQ ID NO.22).

More specifically, the following beta-turns which mimic the RGPG-turn (SEQ ID NO.22) are prepared by the methods disclosed herein:

where X is selected from —NH— (10-membered ring), —NHCH$_2$CH$_2$— (12-membered ring), —NHC(CH$_3$)$_2$CH$_2$— (12-membered ring), —NHC(CH$_3$)$_2$ CH$_2$CH$_2$CH$_2$— (14-membered ring), and —NHC(CH$_3$)$_2$ CH=CHCH$_2$— (14-membered ring).

In addition, beta-turns which mimic the GPGS-turn (SEQ ID NO.23) are prepared in the same manner—that is, conformationally constrained beta-turns of structure 1(a) above are synthesized, where $R^1$=$R^3$=—H, $R^4$=—CH$_2$OH, and X is as disclosed above for the RGPG-turn (SEQ ID NO.22) mimetic.

Once the above family of conformationally constrained reverse-turn mimetics are made, they are assayed using known techniques to determine which construct or constructs most closely mimics the site A loop of influenza (see, e.g., Muller et al., *Vaccine* 8:308-314, 1990; Schulze-Gahmen et al., *Eur. J. Biochem.* 159:283-289, 1986; Satterthwait et al., *Phil. Trans. R. Soc. Lond.* B232:565-572, 1989; Jemmerson et al., *J. Immunol.* 20:579-585, 1990) (which references are hereby incorporated by reference in their entirety).

Having identified one or more conformationally constrained reverse-turn mimetics by the above procedures, a suitable T cell stimulatory peptide is then covalently joined to either the N-terminus or the C-terminus (or both terminuses) of the conformationally constrained reverse-turn mimetic via a cleavable linker using known techniques to yield the peptide vaccine of this invention. With regard to suitable T cell stimulatory peptides, Rothbard and Taylor (*EMBO J.* 7:93, 1988) have previously reported a helper T cell epitope for influenza, and the T cell stimulatory peptide derived from residues 17-31 of the influenza matrix protein (i.e., SGPLKAEIAQRLEDV) (SEQ ID NO.24) is recognized by human cytotoxic T cells (CTL) in association with the MHC class I molecule HLA-A2 (Gotch et al., *Nature* 326:881. 1987). Other suitable T cell stimulatory peptides included those disclosed by DiBrino et al., *J. Immunol.* 151:5930-5935, 1993): NP 44-52 CTELKLSDY (SEQ ID NO.25); PB1 591-599 VSDGGPNLY (SEQ ID NO.26); and NP 265-273 ILRGSVAHK (SEQ ID NO.27).

Example 8

Activity of Peptide Vaccine to Influenza

The immunogenicity of the peptide vaccines of this invention for the influenza virus, including the peptide vaccines of Example 7 above, may generally be determined by employing one or more of the following assays: (1) competition ELISA with a rabbit hyperimmune anti-HA serum and a panel of anti-site A monoclonal antibodies using plates coated with influenza virus strain X-31; (2) decrease in the inhibition of virus-mediated hemagglutination of chick erythrocytes by rabbit hyperimmune anti-HA serum and anti-site A monoclonal antibodies; or (3) inhibition of viral proliferation in MDCK (dog kidney) cells. Such techniques are know to those skilled in this art, and are generally described in Muller et al., Vaccine 8:308-314, 1990 (incorporated herein by reference). The ability of the peptide vaccines of this invention to protect mice against challenge with a mouse-adapted X31 virus strain may be determined by immunization in complete (primary) and incomplete (boost) Freund's adjuvant.

From the foregoing, it will be appreciated that, although specific embodiments of this invention have been described herein for purposes of illustration, various modifications may be made without deviating from the spirit and scope of the invention. Accordingly, the invention is not limited except by the appended claims.

I claim:

1. A compound comprising a conformationally constrained beta-turn mimetic having a C-terminus and an N-terminus, a T cell stimulatory peptide, and a cleavable linker covalently joining at least the C-terminus or the N-terminus of the conformationally constrained beta-turn mimetic to the T cell stimulatory peptide, wherein said conformationally constrained beta-turn mimetic is capable of binding to a B cell such that the compound is internalized by the B cell, and said T cell stimulating peptide is capable of inducing T cell activity when presented on the surface of the B cell following cleavage of the cleavable linker, and wherein the conformationally constrained beta-turn mimetic has the following structure:

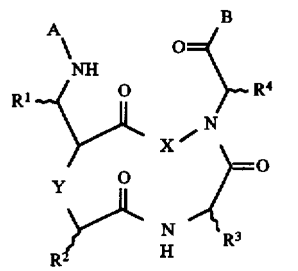

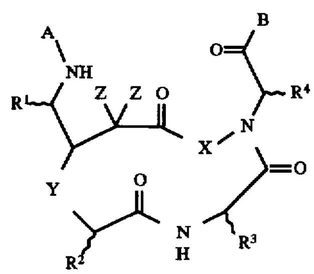

where $R^1$, $R^2$, $R^3$ and $R^4$ are amino acid side chain moieties, X is selected from the chemical moieties identified in Table 1, Y is —$CH_2$—, —NZ—, —O— or —S—, Z is —H or —$CH_3$, A is hydrogen or an amino acid, and B is hydroxyl or an amino acid, wherein said amino acids are the same or different, and at least A or B is an amino acid covalently joined to the T cell stimulating peptide by the cleavable linker and wherein when both A and B are amino acids covalently joined to T cell stimulatory peptides by cleavable linkers, said T cell stimulatory peptides are the same or different.

2. A compound comprising a conformationally constrained gamma-turn mimetic having a C-terminus and an N-terminus, a T cell stimulatory peptide, and a cleavable linker covalently joining at least the C-terminus or the N-terminus of the conformationally constrained gamma-turn mimetic to the T cell stimulatory peptide, wherein said conformationally constrained gamma-turn mimetic is capable of binding to a B cell such that the compound is internalized by the B cell, and said T cell stimulating peptide is capable of inducing T cell activity when presented on the surface of the B cell following cleavage of the cleavable linker, and wherein the conformationally constrained gamma-turn mimetic has the following structure:

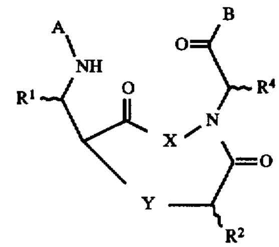

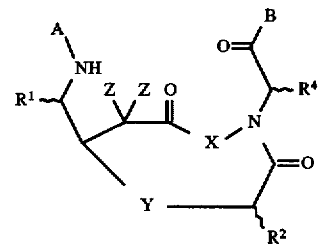

where $R^1$, $R^2$ and $R^4$ are amino acid side chain moieties, X is selected from the chemical moieties identified in Table 1, Y is —$CH_2$—, —NZ—, —O— or —S—, Z is —H or —$CH_3$, A is hydrogen or an amino acid, and B is hydroxyl or an amino acid, wherein said amino acids are the same or different, and at least A or B is an amino acid covalently joined to the T cell stimulating peptide by the cleavable linker, and wherein when both A and B are amino acids covalently joined to T cell stimulatory peptides by cleavable linkers said T cell stimulatory peptides are the same or different.

3. A compound comprising a conformationally constrained beta-bulge mimetic having a C-terminus and an N-terminus, a T cell stimulatory peptide, and a cleavable linker covalently joining at least the C-terminus or the N-terminus of the conformationally constrained beta-bulge mimetic to the T cell stimulatory peptide, wherein said conformationally constrained beta-bulge mimetic is capable of binding to a B cell such that the compound is internalized by the B cell, and said T cell stimulating peptide is capable of inducing T cell activity when presented on the surface of the B cell following cleavage of the cleavable linker, and wherein the conformationally constrained beta-bulge mimetic has the following structure:

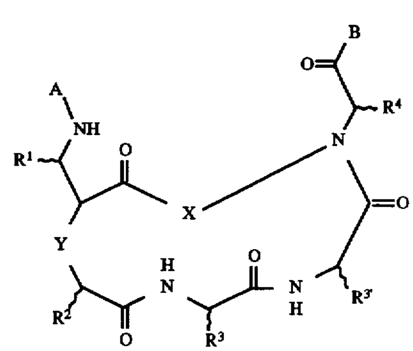

-continued

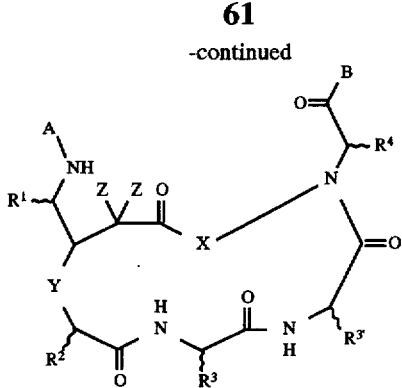

where $R^1$, $R^2$, $R^3$, $R^{3'}$ and $R^4$ are amino acid side chain moieties, X is selected from the chemical moieties identified in Table 1, Y is —$CH_2$—, —NZ—, —O— or —S—, Z is —H or —$CH_3$, A is hydrogen or an amino acid, and B is hydroxyl or an amino acid, wherein said amino acids are the same or different, and at least A or B is an amino acid covalently joined to the T cell stimulating peptide by the cleavable linker, and wherein when both A and B are amino acids covalently joined to T cell stimulatory peptides by cleavable linkers, said T cell stimulatory peptides are the same or different.

4. The compound of any one of claims 1-3 wherein the T cell stimulatory peptide is capable of inducing helper T cell activity when presented on the surface of the B cell in association with a class II MHC molecule.

5. The compound of claim 4 wherein T cell stimulating peptide comprises the amino acid sequence for p24E.

6. The compound of any one of claims 1-3 wherein the cleavable linker is cleavable by Cathepsin D, B or E.

7. The compound of claim 1 wherein the cleavable linker comprises the amino acid sequence FYLKRKR (SEQ ID NO.14).

8. A method for invoking an immune response in a warm-blooded animal to an antigenic region of a pathogenic or non-pathogenic protein, comprising administering to the animal an amount of the compound of any one of claims 1-3 which is effective to induce said immune response to said antigenic region of the protein.

* * * * *